United States Patent
Man et al.

(10) Patent No.: US 10,098,098 B2
(45) Date of Patent: *Oct. 9, 2018

(54) MIXED FATTY ACID SOAP/FATTY ACID INSECTICIDAL, CLEANING, AND ANTIMICROBIAL COMPOSITIONS

(71) Applicant: ECOLAB USA INC., Saint Paul, MN (US)

(72) Inventors: Victor Fuk-Pong Man, St. Paul, MN (US); Yvonne Marie Killeen, South St. Paul, MN (US); Michael Charles DeNoma, Vadnais Heights, MN (US); Kelly J. Herrera, South St. Paul, MN (US); S. John Barcay, Burnsville, MN (US); William J. Pattison, St. Paul, MN (US)

(73) Assignee: Ecolab USA Inc., Saint Paul, MN (US)

( * ) Notice: Subject to any disclaimer, the term of this patent is extended or adjusted under 35 U.S.C. 154(b) by 137 days.

This patent is subject to a terminal disclaimer.

(21) Appl. No.: 13/898,035

(22) Filed: May 20, 2013

(65) Prior Publication Data

US 2013/0253059 A1    Sep. 26, 2013

Related U.S. Application Data

(63) Continuation of application No. 13/306,298, filed on Nov. 29, 2011.

(60) Provisional application No. 61/418,215, filed on Nov. 30, 2010.

(51) Int. Cl.
*A01N 37/02* (2006.01)
*H04W 72/04* (2009.01)

(52) U.S. Cl.
CPC .......... *H04W 72/042* (2013.01); *A01N 37/02* (2013.01)

(58) Field of Classification Search
None
See application file for complete search history.

(56) References Cited

U.S. PATENT DOCUMENTS

| | | | |
|---|---|---|---|
| 3,186,912 A | 6/1965 | Beamer | |
| 4,707,496 A | 11/1987 | Simmons | |
| 4,822,613 A | 4/1989 | Rodero | |
| 5,064,859 A | 11/1991 | Crammer et al. | |
| 5,093,124 A | 3/1992 | Kulenkampff | |
| 5,296,157 A | 3/1994 | MacGlip et al. | |
| 5,296,158 A | 3/1994 | MacGlip et al. | |
| 5,366,995 A * | 11/1994 | Savage et al. | 514/558 |
| 5,424,270 A * | 6/1995 | Winston | 504/101 |
| 5,464,457 A | 11/1995 | Winston et al. | |
| 5,468,715 A | 11/1995 | Joseph et al. | |
| 5,578,250 A | 11/1996 | Thomas et al. | |
| 5,580,567 A | 12/1996 | Roberts | |
| 5,610,130 A | 3/1997 | Thomas et al. | |
| 5,658,954 A | 8/1997 | Targosz | |
| 5,739,172 A * | 4/1998 | Jones | 424/70.22 |
| 5,795,372 A * | 8/1998 | Hill | C23F 11/10 |
| | | | 106/14.13 |
| 5,910,323 A | 6/1999 | Lajoie et al. | |
| 5,939,357 A | 8/1999 | Jones et al. | |
| 6,136,856 A | 10/2000 | Savage et al. | |
| 6,294,577 B1 | 9/2001 | Vander Meer et al. | |
| 6,306,415 B1 | 10/2001 | Reifenrath | |
| 6,582,734 B1 * | 6/2003 | Wei | A01N 59/00 |
| | | | 424/405 |
| 7,470,433 B2 | 12/2008 | Carrara et al. | |
| 7,767,216 B2 | 8/2010 | Baker, Jr. et al. | |
| 7,994,138 B2 | 8/2011 | Awada et al. | |
| 8,080,502 B2 | 12/2011 | Herdt et al. | |
| 8,128,976 B2 | 3/2012 | Man et al. | |
| 8,143,309 B2 | 3/2012 | Awad | |
| 2003/0060379 A1 * | 3/2003 | Souter et al. | 510/131 |
| 2007/0243223 A1 | 10/2007 | Alasri et al. | |
| 2007/0281002 A1 | 12/2007 | Morales et al. | |
| 2008/0051455 A1 | 2/2008 | Achtmann | |
| 2010/0003341 A1 | 1/2010 | Besendorfer | |
| 2010/0112060 A1 | 5/2010 | Maor et al. | |

FOREIGN PATENT DOCUMENTS

| | | |
|---|---|---|
| EP | 0 677 578 | 10/1995 |
| GB | 381290 | 10/1932 |
| GB | 613835 | 12/1948 |
| GB | 1014243 | 12/1965 |
| WO | WO 93/22916 | 11/1993 |
| WO | WO 93/22919 | 11/1993 |
| WO | WO 2007/115691 | 10/2007 |

OTHER PUBLICATIONS

National Pesticide Information Center's General Fact Sheet Potassium Salts of Fatty Acids (created 2001, available at the Oregon State website, web address: npic.orst.edu/factsheets/psfatech.pdf).*
Farrell and Bower "Fatal Water Intoxication," J Clin Pathol. Oct. 2003; 56(10): 803-804.*
Kumar et al. (Pesticide Biochemistry and Physiology vol. 124, Oct. 2015, pp. 48-59).*
ECOLAB USA Inc., PCT/IB2011/055366, filed on Nov. 29, 2011, "International Search Report", dated Jul. 20, 2012.

* cited by examiner

*Primary Examiner* — Kortney L. Klinkel
*Assistant Examiner* — William Y Lee
(74) *Attorney, Agent, or Firm* — McKee, Voorhees & Sease, PLC

(57) ABSTRACT

The present disclosure relates to compositions including a fatty acid soap/fatty acid mixture, and methods of use thereof. The compositions include a C5 to C12 fatty acid or mixtures thereof. The compositions show increased activity, e.g., insecticidal, soil removal, antimicrobial activity, at a controlled pH range of about 7.5 to about 9.0.

20 Claims, 13 Drawing Sheets

MIXED FATTY ACID SOAP/FATTY ACID INSECTICIDAL, CLEANING, AND ANTIMICROBIAL COMPOSITIONS

CROSS-REFERENCE TO RELATED APPLICATIONS

This application is a continuation application of U.S. Ser. No. 13/306,298 filed Nov. 29, 2011, which claims priority under 35 U.S.C. § 119(e) to U.S. Provisional Application entitled "Mixed Fatty Acid Soap/Fatty Acid Insecticidal, Cleaning and Antimicrobial Compositions", Ser. No. 61/418,215, filed on Nov. 30, 2010, which is incorporated herein by reference in its entirety for all purposes.

FIELD OF THE INVENTION

The present disclosure relates generally to fatty acid soap/fatty acid based compositions, and methods of use thereof. In particular, the disclosure relates to a C4 to C12 fatty acid soap/fatty acid based composition. The disclosure also includes methods of using these compositions.

BACKGROUND

Left unattended, insects can quickly infest enclosed structures, such as restaurants and homes. Examples of insects which can infest areas in and around enclosed structures include, for example, cockroaches, ants, fruit flies, houseflies, bed bugs, ground beetles and spiders. In addition to being a nuisance, some of these insects can also bring pathogens into the restaurant or home, creating unsanitary eating and living conditions.

The use of insecticidal compositions has aided in decreasing the infestation of insects in and around residential and commercial structures. Various types of insecticidal compositions and methods of repelling or terminating crawling pests are currently available, including gel baits, glue pads and poisons.

In more recent years, attention has been directed to producing insecticides that are effective and ecologically friendly. In line with this trend, the Environmental Protection Agency (EPA) has issued a list of minimum risk insecticides § 25(b) of the Federal Insecticide, Fungicide, and Rodenticide Act (FIFRA) that are not subject to federal registration requirements because their active and inert ingredients are demonstrated as safe for their intended use. There is an ongoing need to provide effective insecticides which have reduced environmental impact.

SUMMARY

In some aspects, the present invention relates to compositions and methods of use thereof. The compositions and methods may comprise, consist of, or consist essentially of the listed ingredients or steps. As used herein the term "consisting essentially of" shall be construed to mean including the listed ingredients or steps and such additional ingredients or steps which do not materially affect the basic and novel properties of the composition or method.

In some aspects, the present invention relates to an insecticidal composition comprising a fatty acid, a neutralizer, a buffer, and a carrier. The pH of the composition is from about 7.5 to about 9.0. In some embodiments, the fatty acid comprises a branched or straight chain C5 to C12 fatty acid. In other embodiments, the fatty acid is selected from the group consisting of hexanoic acid, heptanoic acid, octanoic acid, nonanoic acid, decanoic acid, lauric acid and mixtures thereof.

In some embodiments, the neutralizer comprises an alkali metal hydroxide. The alkali metal hydroxide may be selected from the group consisting of sodium hydroxide, potassium hydroxide, and mixtures thereof. In other embodiments, the neutralizer is selected from an amine, an alkanolamine, and mixtures thereof.

In other embodiments, the buffer is selected from a weak acid, a weak base, an amphoteric buffering agent, an ampholyte buffering agent, and mixtures thereof. The buffer may be selected from citrate, citric acid, a bicarbonate, and mixtures thereof. In other embodiments, the carrier comprises water.

In some embodiments, the composition comprises about 1.0 wt % to about 10 wt % of the fatty acid; about 1.0 wt % to about 10 wt % of the neutralizer; about 0.1 to about 1.0% of the buffer; and at least about 80 wt % of the carrier. In still yet other embodiments, the compositions further comprise a thickening agent. The thickening agent can be a polymeric or surfactant thickening agent. The thickening agent comprises xanthan gum, guar gum, polyethylene oxide, polyvinyl pyrrolidone, polyvinyl alcohol, clay thickener, betonite, carboxylmethyl ether cellulose, kaolin, soy protein and mixtures thereof.

In still yet other embodiments, the compositions further comprise an additional ingredient selected from an essential oil, 2-phenyl ethyl propionate, a residual insecticide, and mixtures thereof. In still yet other embodiments, the pH of the compositions is about 8.0 to about 8.5.

In some embodiments, the fatty acid comprises decanoic acid, and the neutralizing agent comprises potassium hydroxide.

In some aspects, the present invention relates to methods for eliminating insects. The methods comprise applying to the insects or an area inhabited by the insects an insecticidal composition. The insecticidal compositions comprise a fatty acid; a neutralizer; a buffer; and a carrier, wherein the composition has a pH of about 7.5 to about 9.0.

In other aspects, the present invention relates to methods of reducing a population of microorganism on an object. The methods comprise applying a composition comprising a fatty acid; a neutralizer; a buffer; and a carrier, to the object, wherein the composition has a pH of about 7.5 to about 9.0.

In still yet other aspects, the present invention relates to methods of removing a food soil from a surface. The methods comprise applying a composition comprising a fatty acid; a neutralizer; a buffer; and a carrier, to the surface, wherein the composition has a pH of about 7.5 to about 9.0.

BRIEF DESCRIPTION OF THE DRAWINGS

FIG. 7 is a graphical depiction of the average kill time of 90% (KT-90) of houseflies contacted with various compositions.

DETAILED DESCRIPTION

Figure 1:
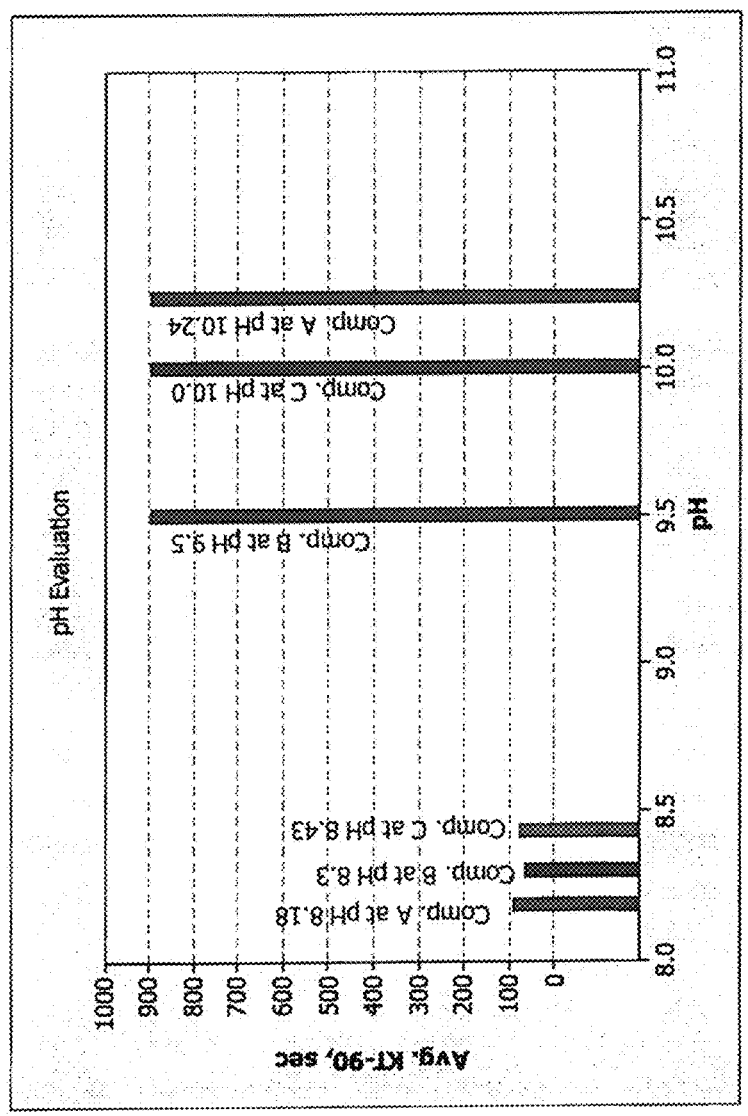
FIG. 1 is a graphical depiction of the effect of pH on the insecticidal efficacy of mixed fatty acid soap/fatty acid compositions.

In some aspects, the present disclosure relates to fatty acid soap/fatty acid compositions and methods of use thereof. The compositions have a variety of uses, for example, as insecticides, soil removers, and as disinfectants/sanitizers. When used at a pH of about 7.5 to about 9.0 the compositions are phase stable and provide improved insecticidal properties than compared to when used at higher pH levels. The compositions also show soil removal properties, e.g., food soil removal, and food contact sanitizing efficacies at this pH level. Without wishing to be bound by any particular theory, it is thought that the insecticidal/soil removal/antimicrobial effects of these compositions is due in part to a very surface active mixture of fatty acid soap/fatty acid, wherein the fatty acid is a minor component that results in improved packing, and improved surface activity.

So that the present disclosure may be better understood, certain terms are first defined.

As used herein, "weight percent," "wt-%," "percent by weight," "% by weight," and variations thereof refer to the concentration of a substance as the weight of that substance divided by the total weight of the composition and multiplied by 100. It is understood that, as used here, "percent," "%," and the like are intended to be synonymous with "weight percent," "wt-%," etc.

As used herein, the term "about" refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

It should be noted that, as used in this specification and the appended claims, the singular forms "a," "an," and "the" include plural referents unless the content clearly dictates otherwise. Thus, for example, reference to a composition containing "a compound" includes a composition having two or more compounds. It should also be noted that the term "or" is generally employed in its sense including "and/or" unless the content clearly dictates otherwise.

As used herein, the phrases "objectionable odor," "offensive odor," or "malodor," refer to a sharp, pungent, or acrid odor or atmospheric environment from which a typical person withdraws if they are able to. Hedonic tone provides a measure of the degree to which an odor is pleasant or unpleasant. An "objectionable odor," "offensive odor," or "malodor" has a hedonic tone rating it as unpleasant as or more unpleasant than a solution of 5 wt-% acetic acid, propionic acid, butyric acid, or mixtures thereof.

As used herein, the term "microorganism" refers to any noncellular or unicellular (including colonial) organism. Microorganisms include all prokaryotes. Microorganisms include bacteria (including cyanobacteria), spores, lichens, fungi, protozoa, virinos, viroids, viruses, phages, and some algae. As used herein, the term "microbe" is synonymous with microorganism.

As used herein, the phrase "food product" includes any food substance that might require treatment with an antimicrobial agent or composition and that is edible with or without further preparation. Food products include meat (e.g. red meat and pork), seafood, poultry, produce (e.g., fruits and vegetables), eggs, living eggs, egg products, ready to eat food, wheat, seeds, roots, tubers, leafs, stems, corns, flowers, sprouts, seasonings, or a combination thereof. The term "produce" refers to food products such as fruits and vegetables and plants or plant-derived materials that are typically sold uncooked and, often, unpackaged, and that can sometimes be eaten raw.

As used herein, the phrase "plant" or "plant product" includes any plant substance or plant-derived substance. Plant products include, but are not limited to, seeds, nuts, nut meats, cut flowers, plants or crops grown or stored in a greenhouse, house plants, and the like. Plant products include many animal feeds.

As used herein, the phrase "meat product" refers to all forms of animal flesh, including the carcass, muscle, fat, organs, skin, bones and body fluids and like components that form the animal. Animal flesh includes, but is not limited to, the flesh of mammals, birds, fishes, reptiles, amphibians, snails, clams, crustaceans, other edible species such as lobster, crab, etc., or other forms of seafood. The forms of animal flesh include, for example, the whole or part of animal flesh, alone or in combination with other ingredients. Typical forms include, for example, processed meats such as cured meats, sectioned and formed products, minced products, finely chopped products, ground meat and products including ground meat, whole products, and the like.

As used herein the term "poultry" refers to all forms of any bird kept, harvested, or domesticated for meat or eggs, and including chicken, turkey, ostrich, game hen, squab, guinea fowl, pheasant, quail, duck, goose, emu, or the like and the eggs of these birds. Poultry includes whole, sectioned, processed, cooked or raw poultry, and encompasses all forms of poultry flesh, by-products, and side products. The flesh of poultry includes muscle, fat, organs, skin, bones and body fluids and like components that form the animal. Forms of animal flesh include, for example, the whole or part of animal flesh, alone or in combination with other ingredients. Typical forms include, for example, processed poultry meat, such as cured poultry meat, sectioned and formed products, minced products, finely chopped products and whole products.

As used herein, the phrase "poultry debris" refers to any debris, residue, material, dirt, offal, poultry part, poultry waste, poultry viscera, poultry organ, fragments or combinations of such materials, and the like removed from a poultry carcass or portion during processing and that enters a waste stream.

As used herein, the phrase "food processing surface" refers to a surface of a tool, a machine, equipment, a structure, a building, or the like that is employed as part of a food processing, preparation, or storage activity. Examples of food processing surfaces include surfaces of food processing or preparation equipment (e.g., slicing, canning, or transport equipment, including flumes), of food processing wares (e.g., utensils, dishware, wash ware, and bar glasses), and of floors, walls, or fixtures of structures in which food processing occurs. Food processing surfaces are found and employed in food anti-spoilage air circulation systems, aseptic packaging sanitizing, food refrigeration and cooler cleaners and sanitizers, ware washing sanitizing, blancher cleaning and sanitizing, food packaging materials, cutting board additives, third-sink sanitizing, beverage chillers and warmers, meat chilling or scalding waters, autodish sanitizers, sanitizing gels, cooling towers, food processing antimicrobial garment sprays, and non-to-low-aqueous food preparation lubricants, oils, and rinse additives.

The term "substantially free" may refer to any component that the composition of the invention or a method incorporating the composition lacks or mostly lacks. When referring to "substantially free" it is intended that the component is not intentionally added to compositions of the invention. Use of the term "substantially free" of a component allows for trace amounts of that component to be included in compositions of the invention because they are present in another component. However, it is recognized that only trace or de minimus amounts of a component will be allowed when the composition is said to be "substantially free" of that component. Moreover, the term if a composition is said to be "substantially free" of a component, if the component is present in trace or de minimus amounts it is understood that it will not affect the effectiveness of the composition. It is understood that if an ingredient is not expressly included herein or its possible inclusion is not stated herein, the invention composition may be substantially free of that ingredient. Likewise, the express inclusion of an ingredient allows for its express exclusion thereby allowing a composition to be substantially free of that expressly stated ingredient.

For the purpose of this patent application, successful microbial reduction is achieved when the microbial populations are reduced by at least about 50%, or by significantly more than is achieved by a wash with water. Larger reductions in microbial population provide greater levels of protection.

As used herein, the term "sanitizer" refers to an agent that reduces the number of bacterial contaminants to safe levels as judged by public health requirements. In an embodiment, sanitizers for use in this invention will provide at least a 99.999% reduction (5-log order reduction). These reductions can be evaluated using a procedure set out in *Germicidal and Detergent Sanitizing Action of Disinfectants*, Official Methods of Analysis of the Association of Official Analytical Chemists, paragraph 960.09 and applicable sections, 15th Edition, 1990 (EPA Guideline 91-2). According to this reference a sanitizer should provide a 99.999% reduction (5-log order reduction) within 30 seconds at room temperature, 25±2° C., against several test organisms.

As used herein, the term "disinfectant" refers to an agent that kills all vegetative cells including most recognized pathogenic microorganisms, using the procedure described in *A.O.A.C. Use Dilution Methods*, Official Methods of Analysis of the Association of Official Analytical Chemists, paragraph 955.14 and applicable sections, 15th Edition, 1990 (EPA Guideline 91-2). As used herein, the term "high level disinfection" or "high level disinfectant" refers to a compound or composition that kills substantially all organisms, except high levels of bacterial spores, and is effected with a chemical germicide cleared for marketing as a sterilant by the Food and Drug Administration. As used herein, the term "intermediate-level disinfection" or "intermediate level disinfectant" refers to a compound or composition that kills mycobacteria, most viruses, and bacteria with a chemical germicide registered as a tuberculocide by the Environmental Protection Agency (EPA). As used herein, the term "low-level disinfection" or "low level disinfectant" refers to a compound or composition that kills some viruses and bacteria with a chemical germicide registered as a hospital disinfectant by the EPA.

As used in this invention, the term "sporicide" refers to a physical or chemical agent or process having the ability to cause greater than a 90% reduction (1-log order reduction) in the population of spores of *Bacillus cereus* or *Bacillus subtilis* within 10 seconds at 60° C. In certain embodiments, the sporicidal compositions of the invention provide greater than a 99% reduction (2-log order reduction), greater than a 99.99% reduction (4-log order reduction), or greater than a 99.999% reduction (5-log order reduction) in such population within 10 seconds at 60° C.

Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can affect two kinds of microbial cell damage. The first is a lethal, irreversible action resulting in complete microbial cell destruction or incapacitation. The second type of cell damage is reversible, such that if the organism is rendered free of the agent, it can again multiply. The former is termed microbiocidal and the later, microbistatic. A sanitizer and a disinfectant are, by definition, agents which provide antimicrobial or microbiocidal activity. In contrast, a preservative is generally described as an inhibitor or microbistatic composition As used herein, the term "alkyl" or "alkyl groups" refers to saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups).

Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including hetero aromatic) groups.

In some embodiments, substituted alkyls can include a heterocyclic group. As used herein, the term "heterocyclic group" includes closed ring structures analogous to carbocyclic groups in which one or more of the carbon atoms in the ring is an element other than carbon, for example, nitrogen, sulfur or oxygen. Heterocyclic groups may be saturated or unsaturated. Exemplary heterocyclic groups include, but are not limited to, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan.

Compositions

In some aspects, the compositions include a fatty acid soap/fatty acid mixture. The compositions include a fatty acid, a neutralizer, a buffer, and a carrier. Optionally, the compositions can also include additional functional ingredients. The compositions can function as insecticides, food soil removal agents, and antimicrobial agents, among other uses.

Fatty Acids

In some aspects, the compositions include one or more fatty acid. As used herein, the term "fatty acid" includes any of a group of carboxylic acids that include a long alkyl chain. In some embodiments, the alkyl groups can be linear or branched, and saturated or unsaturated. The chain of alkyl groups contain from 4 to 12 carbon atoms, 5 to 11 carbon atoms, or 8 to 10 carbon atoms.

In some embodiments, a C4 to C12 branched or straight chain fatty acid is included in the compositions. In some embodiments, the compositions are substantially free of, or free of, fatty acids with a chain length greater than C12. For example, in some embodiments, the compositions are free of, or substantially free of, C14 to C24 fatty acids.

The fatty acid can be selected from hexanoic acid, heptanoic acid, octanoic acid, nonanoic acid, decanoic acid, lauric acid and mixtures thereof. In some embodiments, two or more fatty acids can be used. For example, a mixture of a C8 and a C10 fatty acid can be used. In other embodiments, the fatty acid includes decanoic acid. Decanoic acid has the formula $CH_3(CH_2)_8COOH$, and is a saturated fatty acid.

In some embodiments, the fatty acid is present in the compositions at an amount of about 1.0 wt % to about 10 wt %, about 3 wt % to about 8 wt %, or about 5 wt % to about 7 wt %. It is to be understood that all ranges and values between these ranges and values are encompassed by the present compositions.

Surprisingly, it has been found that when used at a pH of between about 7.5 and about 9.0, or about 8.0 and about 8.5, the compositions have improved insecticidal, cleaning, and/or sanitizing properties, and are phase stable. Without wishing to be bound by any particular theory, it is thought that at lower pH levels, phase separation occurs as there is more fatty acid present than can be coupled by the fatty acid soap present. At higher pH levels, e.g., a pH greater than about 9.0, it is thought that the level of fatty acid soap present will be too high. It is thought that this high level of fatty acid soap decreases the surface activity of the compositions, e.g., wetting ability of the compositions.

Neutralizers

In some aspects, the compositions include a neutralizer. The neutralizer can be included to neutralize a portion of the fatty acid, thereby forming a fatty acid soap. In some embodiments, the neutralizer includes an alkali metal hydroxide, including but not limited to, sodium hydroxide, potassium hydroxide, and mixtures thereof. In other embodiments, the neutralizer includes an amine or an alkanolamine. Examples of amines, or alkanolamines suitable for use with the present compositions include, but are not limited to, monoethanolamine, diethanolamine, triethanolamine, monoisopropanolamine, monoisopropylamine, isopropylamine, n-propylamine, diethyleneamine, thriethylamine, n-butylamine, isobutylamine, cyclohexylamine, and mixtures thereof.

In some embodiments, the neutralizer is present in an amount effective to provide about 5 wt % to about 10 wt % of the fatty acid soap from the fatty acid. The neutralizer can be present in the compositions at an amount of about 1.0 wt % to about 10 wt %, about 3 wt % to about 8 wt %, or about 5 to about 7 wt %. It is to be understood that all ranges and values between these ranges and values are encompassed by the present compositions.

Buffer

In some aspects, the compositions include a buffer to stabilize the pH of the compositions. Suitable buffers include weak acids, weak bases, ampholytes and mixtures thereof. In some embodiments, the buffer can include, but is not limited to, carbonates, bicarbonates, citric acid and citrate. The term "carbonate" includes, for example, sodium carbonate, potassium carbonate, sesquicarbonate, and mixtures thereof. The term "bicarbonate" includes, for example, sodium bicarbonate, potassium bicarbonate, and mixtures thereof. The term "citrate" includes, for example, sodium citrate, potassium citrate, and mixtures thereof.

The compositions can include about 0.1 wt % to about 10 wt %, about 0.5 wt % to about 5 wt %, or about 1 wt % of a buffer, or mixture of buffers. It is to be understood that all values and ranges between these values and ranges are encompassed by the compositions.

Carrier

In some aspects, the compositions also include a carrier. In some embodiments, the carrier includes water. In other embodiments, a water-soluble solvent, such as alcohols and polyols, can be used as a carrier. These solvents may be used alone or with water. Some examples of suitable alcohols include methanol, ethanol, propanol, butanol, and the like, as well as mixtures thereof. Some examples of polyols include glycerol, ethylene glycol, propylene glycol, diethylene glycol, and the like, as well as mixtures thereof. The carrier selected can depend on a variety of factors, including, but not limited to the desired functional properties of the compositions, and/or the intended use of the compositions.

In some embodiments, the compositions are not meant to be diluted, but are rather ready to use solutions. In some embodiments, the compositions can include at least about 80 wt %, at least about 85 wt %, at least about 90 wt %, or at least about 95 wt % of a carrier. It is to be understood that all ranges and values between these ranges and values are included in the present compositions.

Additional Functional Ingredients

The compositions may also include additional components or agents, such as additional functional ingredients. The functional materials provide desired properties and functionalities to the compositions. For the purpose of this application, the term "functional materials" includes a material that when dispersed or dissolved in a use and/or concentrate solution, such as an aqueous solution, provides a beneficial property in a particular use. Some particular examples of functional materials are discussed in more detail below, although the particular materials discussed are given by way of example only, and a broad variety of other functional materials may be used.

The compositions may also include a thickening agent. Thickening agents can be added to the compositions to reduce the misting of the compositions. Thickening agents suitable for use in the present compositions include, but are not limited to, xanthan gum, guar gum, polyethylene oxide, polyvinyl pyrrolidone, polyvinyl alcohol, clay thickener, betonite, carboxylmethyl ether cellulose, kaolin, soy protein and mixtures thereof. When a thickening agent is included in the compositions, the thickening agent may constitute between about 0.01 wt % and about 1.0 wt %, about 0.05 wt % and about 0.5 wt %, or about 0.1 wt % of the compositions.

The compositions may also include an additional ingredient selected from an essential oil, 2-phenyl ethyl propionate, a residual insecticide (viz. an insecticide that is efficacious even after drying), and mixtures thereof. The compositions may also include an additional insecticide, for example, a reduced risk pesticide as classified by the Environmental Protective Agency. Reduced risk pesticides include pesticides with characteristics such as very low toxicity to humans and non target organisms, including fish and birds, low risk of ground water contamination or runoff, and low potential for pesticide resistance. Exemplary active ingredients for reduced risk pesticides include but are not limited to, castor oil, cedar oil, cinnamon and cinnamon oil, citric acid, citronella and citronella oil, cloves and clove oil, corn gluten meal, corn oil, cottonseed oil, dried blood, eugenol, garlic and garlic oil, geraniol, geranium oil, lauryl sulfate, lemon grass oil, linseed oil, malic acid, mint and mint oil, peppermint and peppermint oil, 2-phenethyl propionate (2-phenyethyl propionate), potassium sorbate, putrescent whole egg solids, rosemary and rosemary oil, sesame and sesame oil, sodium chloride, sodium lauryl sulfate, soybean oil, thyme and thyme oil, white pepper, zinc metal strips, and combinations thereof.

The compositions may also include attractants such as cockroach pheromones (e.g., sex attractants, aggregation pheromones) or food-based attractants (e.g., methylcyclopentenalone, maltol, fenugreek and other flavorings). When an attractant is included in the compositions, the attractant may constitute between about 0.1% and about 5% by weight of a use solution of the composition.

The compositions may also optionally include humectants such as glycerol to slow evaporation and maintain wetness of the compositions after application. When a humectant is included in the compositions, the humectant may constitute between about 0.5% and about 10% by weight of the compositions.

The compositions may also optionally include a foaming agent. When a foaming agent is included in the compositions, the foaming agent may constitute between about 1% and about 10% by weight of the pesticide composition. In other embodiments, the compositions do not include a foaming agent.

Methods of Use

The compositions have numerous uses. For example, the compositions can be used as insecticides, soil removal compositions, and/or antimicrobial compositions. Additionally, the compositions can be used as floor strippers, antibacterial lubricants etc.

Insecticides

In some aspects, the present compositions can be used as insecticides. Surprisingly, it has been found that when used in a controlled pH range of about 7.5 to about 9.0, the compositions show highly efficacious insecticidal properties. The compositions are effective against a broad range of insects, including, but not limited to: cockroaches, e.g., German cockroaches, American cockroaches; bed bugs; flies, e.g., house flies, fruit flies; ants, e.g., odorous house ants, pharaoh ants, argentine ants; and spiders. Without wishing to be bound by any particular theory, it is thought that the compositions are highly effective insecticides due in part to their wetting abilities. That is, it is thought that the compositions enter the spiracles of the insects contacted, and rapidly suffocate the insects. It is also thought, that due to the wetting abilities of the compositions, the compositions enter the insects through the spiracles, and kills the insects by upsetting their internal chemical balance.

In some embodiments, the compositions include a fatty acid soap/fatty acid mixture including potassium decanoate/decanoic acid. In some embodiments, the compositions include about 1.0 to about 10 wt % of the fatty acid soap, or about 5 wt % to about 8 wt % of the fatty acid soap. This particular fatty acid soap/fatty acid mixture has been found to provide rapid kill against most insects when used at a pH of about 7.5 to about 9.0, or about 8.0 to about 8.5. For example, it has been found that this composition kills about 90% of German cockroaches contacted in less than about 100 seconds.

In some embodiments, when formulated as an insecticide, the compositions include only ingredients listed on the EPA 25(B) exempt list. Additionally, the compositions may include only "food additive" ingredients. The term "food additive" means that a composition or chemical may be suitable for human consumption. In the food and beverage industry, it may be desirable that any composition or chemical that comes into contact with foods and beverages for human consumption, be suitable for human consumption. Thus, every chemical that makes up a composition would have to be suitable for human consumption.

When used as an insecticide, the compositions may be applied onto a surface as a spray or foam. The compositions are applied onto the surface for an amount of time sufficient to terminate the insects. The insecticide compositions can be applied in and around areas such as apartment buildings, bakeries, beverage plants, bottling facilities, breweries, cafeterias, candy plants, canneries, cereal processing and manufacturing plants, cruise ships, dairy barns, poultry facilities, flour mills, food processing plants, frozen food plants, homes hospitals, hotels, houses, industrial buildings, kennels, kitchens, laboratories, manufacturing facilities, mausoleums, meat processing and packaging plants, meat and vegetable canneries, motels, nursing homes, office buildings, organic facilities, restaurants, schools, stores, supermarkets, warehouses and other public buildings and similar structures. In particular, the compositions can be applied to surfaces, such as floors, where pests may harbor, including cracks, crevices, niches, dark areas, drains, and other harborage sites.

The compositions may also be directly applied to the insects. The compositions may be applied to insects by any suitable application method, including but not limited to, by spraying, or foaming the compositions on to the insects.

Soil Removal

In some aspects, the compositions can be used to remove soil from a surface. For example, the compositions can be used to remove a food soil from a surface. The methods include contacting the surface with the compositions such that the soil is removed. Contacting can include any of numerous methods for applying a composition, such as spraying the composition on to the object, immersing the object in the composition, or a combination thereof. The compositions can be applied in a variety of areas including kitchens, bathrooms, factories, hospitals, dental offices and food plants, and can be applied to a variety of hard surfaces having smooth, irregular or porous topography. The compositions can be applied to or brought into contact with an object by any conventional method or apparatus for applying a cleaning composition to an object. For example, the object can be wiped with, sprayed with, and/or immersed in the composition, or a use solution made from the composition. The compositions can be sprayed, or wiped onto a surface; the compositions can be caused to flow over the surface, or the surface can be dipped into the composition. Contacting can be manual or by machine.

Exemplary articles that can be treated, i.e., cleaned, with the compositions include, but are not limited to motor vehicle exteriors, textiles, food contacting articles, clean-in-place (CIP) equipment, health care surfaces and hard surfaces. Exemplary motor vehicle exteriors include cars, trucks, trailers, buses, etc. that are commonly washed in commercial vehicle washing facilities. Exemplary textiles include, but are not limited to, those textiles that generally are considered within the term "laundry" and include clothes, towels, sheets, etc. In addition, textiles include curtains. Exemplary food contacting articles include, but are not limited to, dishes, glasses, eating utensils, bowls, cooking articles, food storage articles, etc. Exemplary CIP equipment includes, but is not limited to, pipes, tanks, heat exchangers, valves, distribution circuits, pumps, etc. Exemplary health care surfaces include, but are not limited to, surfaces of medical or dental devices or instruments. Exemplary hard surfaces include, but are not limited to, floors, counters, glass, walls, etc. Hard surfaces can also include the inside of dish machines, and laundry machines. In general, hard surfaces can include those surfaces commonly referred to in the cleaning industry as environmental surfaces. Such hard surfaces can be made from a variety of materials including, for example, ceramic, metal, glass, wood or hard plastic.

Antimicrobial Uses

In some aspects, the compositions may used to reduce a population of microorganisms from an object. The method includes applying the compositions to the object, such that the population of microorganism is reduced.

The compositions can be used for a variety of domestic or industrial applications, e.g., to reduce microbial or viral populations on a surface or object or in a body or stream of water. The compositions can be applied in a variety of areas including kitchens, bathrooms, factories, hospitals, dental offices and food plants, and can be applied to a variety of hard or soft surfaces having smooth, irregular or porous topography. Suitable hard surfaces include, for example, architectural surfaces (e.g., floors, walls, windows, sinks, tables, counters and signs); eating utensils; hard-surface medical or surgical instruments and devices; and hard-surface packaging. Such hard surfaces can be made from a variety of materials including, for example, ceramic, metal, glass, wood or hard plastic. Suitable soft surfaces include, for example paper; filter media; hospital and surgical linens and garments; soft-surface medical or surgical instruments and devices; and soft-surface packaging. Such soft surfaces can be made from a variety of materials including, for example, paper, fiber, woven or nonwoven fabric, soft plastics and elastomers. The compositions can also be applied to soft surfaces such as food and skin (e.g., a hand). The present compositions can be employed as a foaming or nonfoaming environmental sanitizer or disinfectant.

The compositions can also be used on foods and plant species to reduce surface microbial populations; used at manufacturing or processing sites handling such foods and plant species; or used to treat process waters around such sites. For example, the compositions can be used on food transport lines (e.g., as belt sprays); boot and hand-wash dip-pans; food storage facilities; anti-spoilage air circulation systems; refrigeration and cooler equipment; beverage chillers and warmers, blanchers, cutting boards, third sink areas, and meat chillers or scalding devices. The compositions can be used to treat produce transport waters such as those found in flumes, pipe transports, cutters, slicers, blanchers, retort systems, washers, and the like. Particular foodstuffs that can be treated with compounds of the invention include eggs, meats, seeds, leaves, fruits and vegetables. Particular plant surfaces include both harvested and growing leaves, roots, seeds, skins or shells, stems, stalks, tubers, corms, fruit, and the like. The compositions may also be used to treat animal carcasses to reduce both pathogenic and non-pathogenic microbial levels.

The compositions can be applied to microbes or to soiled or cleaned surfaces using a variety of methods. These methods can operate on an object, surface, in a body or stream of water or a gas, or the like, by contacting the object, surface, body, or stream with a compound of the invention. Contacting can include any of numerous methods for applying a composition, such as spraying the composition, immersing the object in the composition, foam or gel treating the object with the composition, or any combination thereof.

A composition can be applied to or brought into contact with an object by any conventional method or apparatus for applying an antimicrobial or cleaning composition to an object. For example, the object can be wiped with, sprayed with, foamed on, and/or immersed in the composition, or a use solution made from the composition. The composition can be sprayed, foamed, or wiped onto a surface; the composition can be caused to flow over the surface, or the surface can be dipped into the composition. Contacting can be manual or by machine. Food processing surfaces, food products, food processing or transport waters, and the like can be treated with liquid, foam, gel, aerosol, gas, wax, solid, or powdered stabilized compositions.

Those skilled in the art will recognize, or be able to ascertain using no more than routine experimentation, numerous equivalents to the specific procedures, embodiments, claims, and examples described herein. Such equivalents are considered to be within the scope of this invention and covered by the claims appended hereto. The contents of all references, patents, and patent applications cited throughout this application are hereby incorporated by reference. The invention is further illustrated by the following examples, which should not be construed as further limiting.

EXAMPLES

Example 1

A study was run to determine the effect of pH on the insecticidal effectiveness of exemplary compositions. The following compositions were tested.

TABLE 1

| Ingredient | Composition A (wt %) | Composition B (wt %) | Composition C (wt %) |
|---|---|---|---|
| Soft water | 86.65 | 87.65 | 88.65 |
| Buffer | 1.00 | 1.00 | 1.00 |
| Fatty acid | 6.00 | 6.00 | 6.00 |
| Neutralizer | 4.35 | 4.35 | 4.35 |
| 2-phenylethyl propionate | 1.00 | 1.00 | 0 |
| Peppermint Oil | 1.00 | 0 | 0 |
| Total | 100 | 100 | 100 |
| Percent Fatty Acid Soap Formed | 7.32 | 7.32 | 7.32 |

Each of compositions A, B and C were tested for their ability to kill cockroaches. Compositions A and B were also tested at various pH levels. For this study, the kill time was measured as time in seconds for 90% of cockroaches to die after exposure to the test compositions (KT-90) in a jar. The KT-90 results are shown in the table below for each of the test compositions at various pH levels.

TABLE 2

| | KT-90 (seconds) | | | | | |
|---|---|---|---|---|---|---|
| | Composition A at pH 8.18 | Composition A at pH 10.24 | Composition B at pH 8.3 | Composition B at pH 9.5 | Composition B at pH 10 | Composition C at pH 8.43 |
| | 90 | >900 | 63 | >900 | >900 | 76 |
| | 90 | | | | | |
| | 85 | | | | | |

These results are also graphically depicted in FIG. 1. As can be seen from this table and FIG. 1, the compositions tested with a pH between 8.0 and 8.5 had a much lower KT-90 compared to those compositions with a pH higher than 9.0. That is, the compositions with a pH between 8.0 and 8.5 had a greater ability to kill cockroaches in a shorter amount of time.

Without wishing to be bound by any particular theory, it is thought that it is the fatty acid/fatty acid soap at the optimum pH which was responsible for killing the cockroaches.

Another study was run to evaluate the effect of pH versus kill time (KT-90). For this experiment the same base formula was used, and the pH was adjusted using either citric acid (to make the compositions more acidic) or neutralizer (to make the compositions more basic). The table below shows the compositions used for this study.

TABLE 3

| Ingredient | Comp. D (wt %) | Comp. E (wt %) | Comp. F (wt %) | Comp. G (wt %) | Comp. H (wt %) | Comp. I (wt %) | Comp. J (wt %) | Comp. K (wt %) |
|---|---|---|---|---|---|---|---|---|
| Soft water | 87.65 | 87.65 | 87.65 | 87.65 | 87.65 | 87.65 | 87.65 | 87.65 |
| Buffer | 1.00 | 1.00 | 1.00 | 1.00 | 1.00 | 1.00 | 1.00 | 1.00 |
| Fatty acid | 6.00 | 6.00 | 6.00 | 6.00 | 6.00 | 6.00 | 6.00 | 6.00 |
| Neutralizer | 4.35 | 4.35 | 4.35 | 4.35 | 4.35 | 4.35 | 4.35 | 4.35 |
| 2-phenylethyl propionate | 1.00 | 1.00 | 1.00 | 1.00 | 1.00 | 1.00 | 1.00 | 1.00 |
| Total | 100 | 100 | 100 | 100 | 100 | 100 | 100 | 100 |
| Percent Fatty Acid Soap Formed | 7.32 | 7.32 | 7.32 | 7.32 | 7.32 | 7.32 | 7.32 | 7.32 |
| pH | 5.20 | 7.42 | 8.20 | 8.53 | 9.01 | 9.61 | 9.90 | 11.25 |

The phase stability of this composition at the various pH levels tested was recorded, as was the KT-90. The results of this study are shown in the table below.

TABLE 4

| | Comp. D | Comp. E | Comp. F | Comp. G | Comp. H | Comp. I | Comp. J | Comp. K |
|---|---|---|---|---|---|---|---|---|
| Phase Stability | Phase separation | White opaque mini-emulsion | Clear | Clear | Clear | Clear | Clear | Clear |
| KT-90 Seconds | 107 | 58 | 61 | 74 | 300 | 600 | >900 | >900 |

Figure 2:
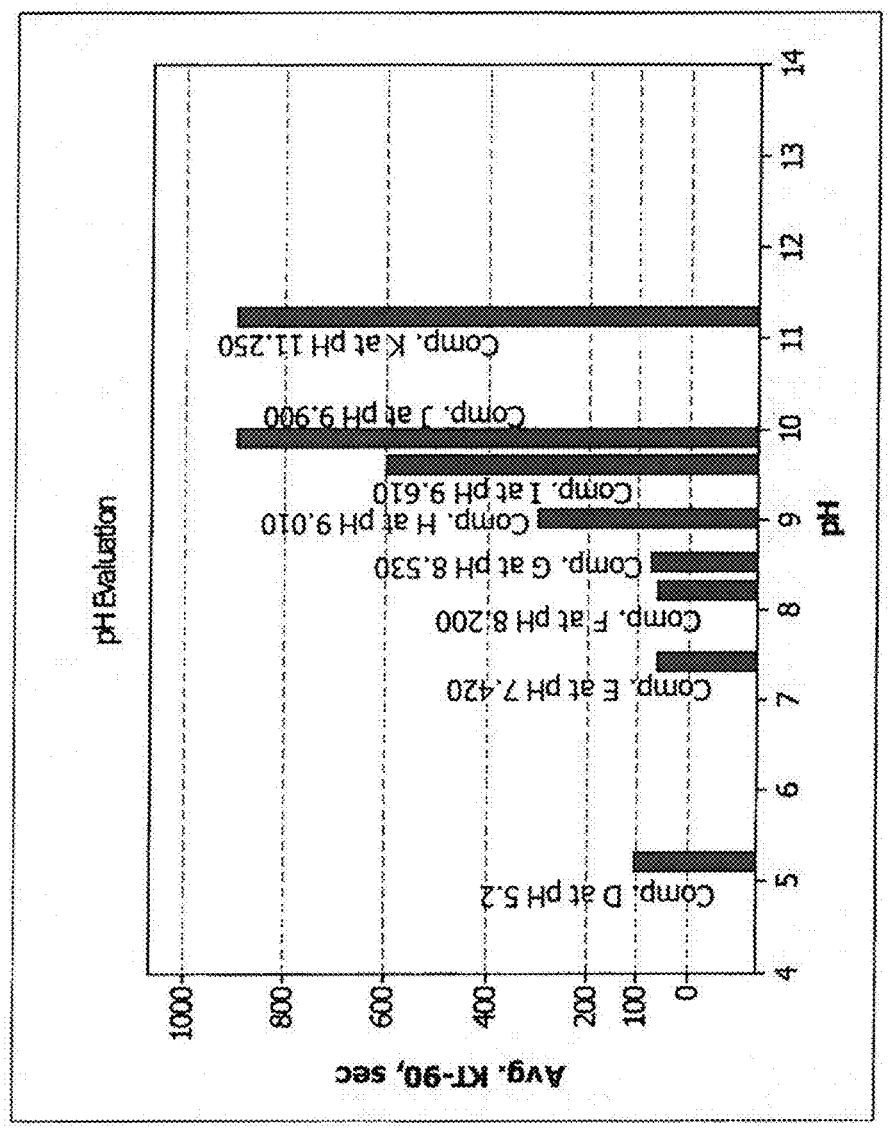
FIG. 2 is a graphical depiction of the effect of pH on the insecticidal efficacy of mixed fatty acid soap/fatty acid compositions.

The results from this study are also shown in FIG. 2. As can be seen from these results, the compositions tested with a pH below 8.5 had a much faster KT-90. However, at an acidic pH (Compositions D and E), the compositions were not stable. Thus, at about pH 7.5 to about 8.5 the compositions tested were both phase stable, and had low KT-90 scores.

Example 2

A study was performed to evaluate the effect of pH on the wetting abilities of test compositions. For this study, the contact angle of test compositions at various pH levels and at various times, was measured on American cockroach wings. The compositions tested each had 7.25% of a fatty acid soap, 1% phenylethyl proprionate, 1% sodium citrate, and 0.10% xanthan gum. The pH of each of the test solutions was adjusted to either 8.3, 11.5, or 6.7. Water was also used as a control. The results are shown in the table below:

TABLE 5

| pH | Composition Tested | Contact Angle at 1 second | Contact Angle at 30 seconds | Contact Angle at 60 seconds |
|---|---|---|---|---|
| 8.3 | 7.25% fatty acid soap, 1% phenylethyl proprionate, 1% sodium citrate, 0.10% xanthan gum | 18.48 | 1.16 | 1.93 |
| 8.3 | 7.25% fatty acid soap, 1% phenylethyl proprionate, 1% sodium citrate, 0.10% xanthan gum | 15.61 | | 1.22 |
| Average | | 17.045 | 1.16 | 1.575 |
| 11.5 | 7.25% fatty acid soap, 1% phenylethyl proprionate, 1% sodium citrate, 0.10% xanthan gum | 26.81 | 19.44 | 20.93 |
| 11.5 | 7.25% fatty acid soap, 1% phenylethyl proprionate, 1% sodium citrate, 0.10% xanthan gum | 31.91 | 22.48 | 21.49 |
| Average | | 29.36 | 20.96 | 21.21 |
| 6.7 | 7.25% fatty acid soap, 1% phenylethyl proprionate, 1% sodium citrate, 0.10% xanthan gum | Drop soaked into wings immediately | | |
| 6.7 | 7.25% fatty acid soap, 1% phenylethyl proprionate, 1% sodium citrate, 0.10% xanthan gum | Drop soaked into wings immediately | | |
| Average | | N/A | N/A | N/A |
| | Water | 58.33 | 51.07 | 51.62 |
| | Water | 73.03 | 65.25 | 61.22 |
| | Water | 58.81 | 44.99 | 47.64 |
| Average | | 63.39 | 53.77 | 53.49 |

Figure 3:
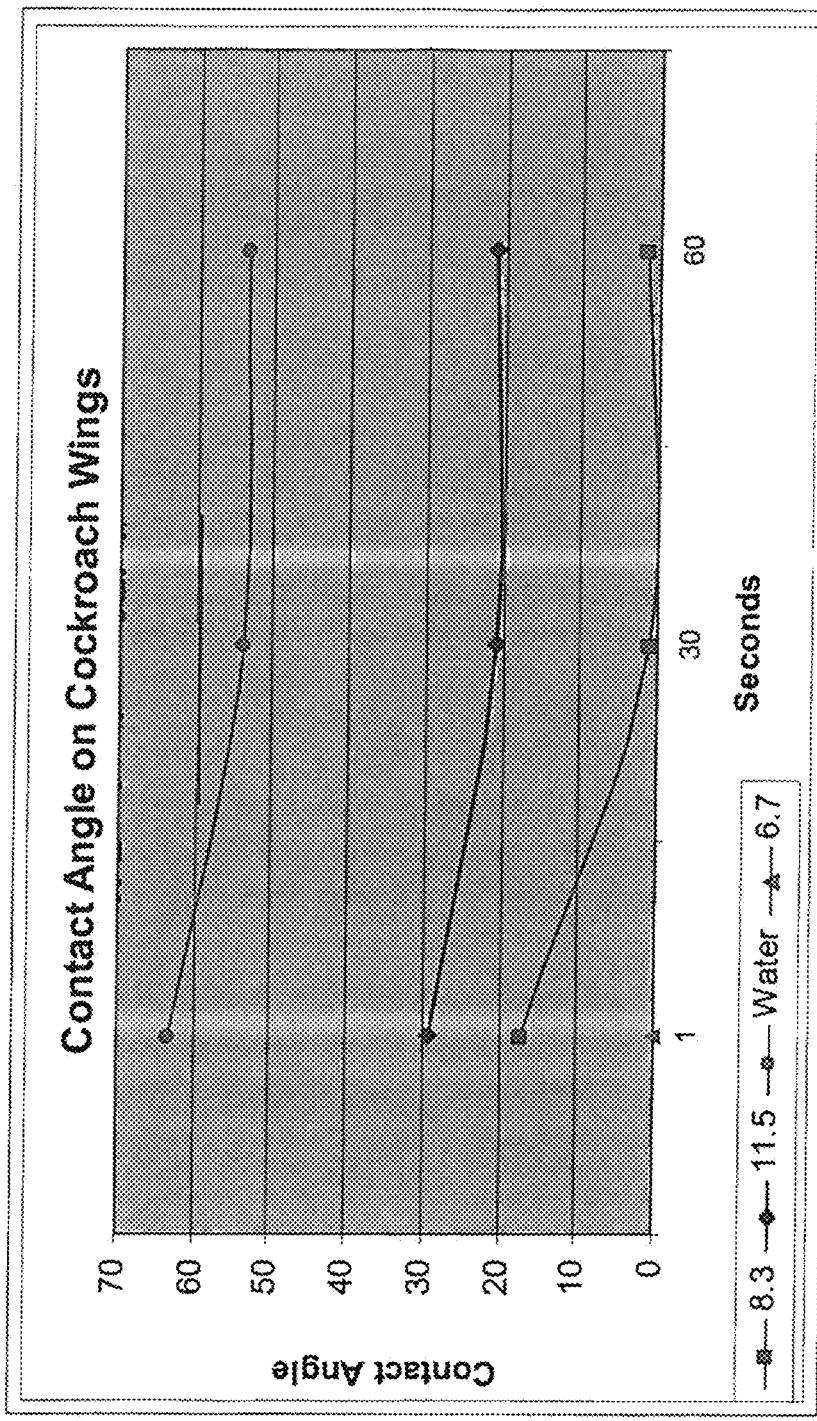
FIG. 3 is a graphical depiction of the effect of pH on the contact angle of mixed fatty acid soap/fatty acid compositions.

These results are also shown in FIG. 3. As can be seen from these results, both the test compositions at pH 6.7 and 8.3 completely wet the wings by 30 seconds. By "completely wet" it is meant that a contact angle of zero degrees (0°) was measured. As is also seen, the same composition at a higher pH did not wet the wings completely even after sixty seconds. Without wishing to be bound by any particular theory, it is thought that a lower contact angle results in a higher kill. That is, it is thought that better wetting compositions wet the highly hydrophobic exoskeleton of insects, covering the spiracles of the insects, thereby suffocating them. It is also thought that a high wetting composition leads to a higher kill rate, as the better wetting a composition is, the more chemicals that will enter into the insects through the spiracles.

Example 3

A study was performed to measure the food soil removal abilities of test compositions. For this study, white vinyl tiles from Flexco were soiled with red soil. The red soil used for this study was a mixture of lard, corn oil, whole powdered egg, and iron oxide. The tiles were "painted" with the red soil using a 3 inch foam brush to form a uniform coating or layer. Then the tiles were left to dry for 24 hours before testing.

To determine the percent (%) soil removal (SR), the reflectance of the tile sample was measured on a spectrophotometer. The "L value" is a direct reading supplied by the spectrophotometer. L generally is indicative of broad visible spectrum reflectance, where a value of 100% would be absolute white. The % soil removal is calculated from the difference between the initial (before cleaning) lightness (L) value and the final L value (after cleaning):

$$SR = ((L_{final} - L_{initial})/(L_{unsoiled\ tile} - L_{initial})) \times 100\%$$

Two compositions were tested for soil removal. The compositions are show in the table below:

TABLE 5a

| Ingredient | Comp. L (wt %) | Comp. Q (wt %) |
|---|---|---|
| Soft water | 88.18 | 87.74 |
| Buffer | 1 | 1.5 |
| Fatty acid | 6 | 5.9 |
| Neutralizer | 3.72 | 4.76 |
| 2-phenylethyl propionate | 1 | |
| Thickener | 0.1 | 0.1 |

The test compositions were compared to a commercially available cleaner, Orange Force®, commercially available from Ecolab Inc. located in St. Paul, Minn. and Formula 409 commercially available from Clorox Company located in Pleasanton, Calif.

Figure 4:
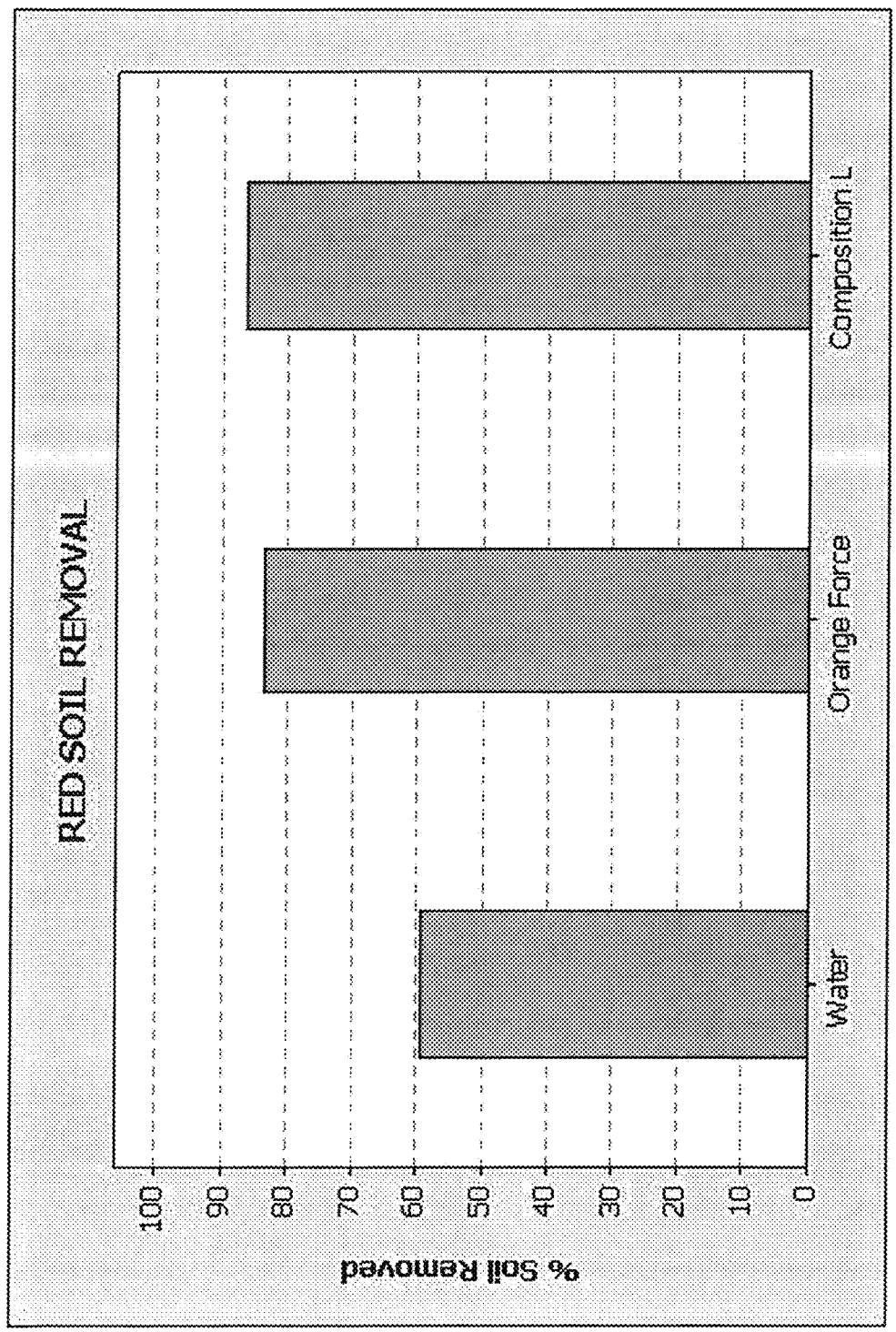
FIG. 4 is a graphical depiction of the soil removal capabilities of mixed fatty acid soap/fatty acid compositions, and comparative compositions.
Figure 4A:
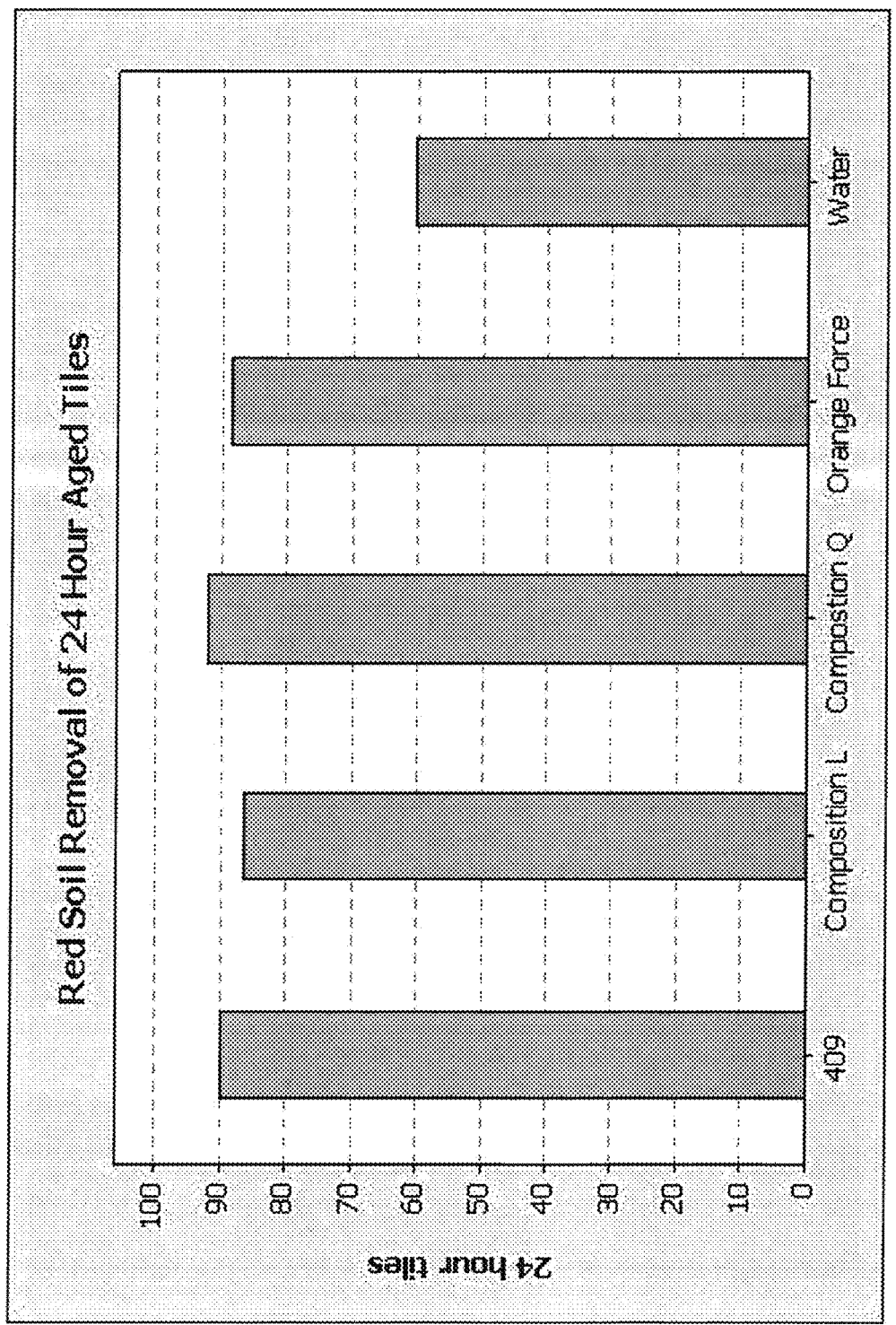
FIG. 4a is a graphical depiction of the soil removal capabilities of mixed fatty acid soap/fatty acid compositions, and comparative compositions on soil aged 24 hours.

The results of this study are shown in FIGS. 4 and 4a. As can be seen from this Figure, test composition Q removed slightly more of the red soil than the other products tested.

Results provided in FIG. 4a shows that on 24 hour aged tiles, test composition Q removes considerably more soil than the other products tested. Thus, it was shown that exemplary compositions can also be used for soil removal.

Example 4

Test compositions were evaluated for their food contact sanitizing ability. In particular, the test compositions were evaluated against *Escherichia coli* ATCC 11229 and *Staphyloccoccus aureus* ATCC 6538. Four test compositions were used for this test. The compositions are shown in the table below.

TABLE 6

| Ingredient | Comp. L (wt %) | Comp. M (wt %) | Comp. P (wt %) | Comp. Q (wt %) |
|---|---|---|---|---|
| Soft water | 88.18 | 87.24 | 88.06 | 87.74 |
| Buffer | 1.00 | 1.357 | 1.51 | 1.50 |
| Fatty acid | 6.00 | 6.00 | 5.99 | 5.90 |
| Neutralizer | 3.72 | 4.3 | 4.34 | 4.76 |
| 2-phenylethyl propionate | 1.00 | 1.00 | | |
| Thickener | 0.1 | | 0.10 | 0.10 |

The compositions were tested against *Escherichia coli* ATCC 11229 and *Staphyloccoccus aureus* ATCC 6538, at ambient temperature for 30 and 60 second exposure times. The results are shown below.

TABLE 7

Inoculum Numbers (CFU/mL) for Compositions L & M

| Test System | A | B | Average |
|---|---|---|---|
| *Escherichia coli* ATCC 11229 | 144 × 10$^6$ | 162 × 10$^6$ | 1.5 × 10$^8$ |
| *Staphyloccoccus aureus* ATCC 6538 | 57 × 10$^6$ | 74 × 10$^6$ | 6.6 × 10$^7$ |

TABLE 7a

Inoculum Numbers (CFU/mL) for Compositions P

| Test System | A | B | Average |
|---|---|---|---|
| *Escherichia coli* ATCC 11229 | 198 × 10$^6$ | 190 × 10$^6$ | 1.9 × 10$^8$ |
| *Staphylococcus aureus* ATCC 6538 | 63 × 10$^6$ | 77 × 10$^6$ | 7.0 × 10$^7$ |

TABLE 8

Inoculum Numbers (CFU/mL) for Composition Q

| Test System | A | B | Average |
|---|---|---|---|
| *Staphylococcus aureus* ATCC 6538 | 98 × 10$^6$ | 79 × 10$^6$ | 8.9 × 10$^7$ |
| *Escherichia coli* ATCC 11229 | 70 × 10$^6$ | 80 × 10$^6$ | 7.5 × 10$^7$ |

TABLE 9

*Escherichia coli* ATCC 11229

| Test Composition | Exposure Time (seconds) | Survivors (CFU/mL) | Average Survivors (CFU/mL) | Log Reduction | Percent Reduction |
|---|---|---|---|---|---|
| Composition L | 30 | <10, <10 | <10 | >7.18 | >99.999 |
| Composition L | 60 | <10, <10 | <10 | >7.18 | >99.999 |
| Composition M | 30 | <10, <10 | <10 | >7.18 | >99.999 |
| Composition M | 60 | <10, <10 | <10 | >7.18 | >99.999 |
| Composition P | 30 | <10, <10 | <10 | >7.29 | >99.999 |
| Composition P | 60 | 1.0 × 10$^1$, <10 | <10 | >7.29 | >99.999 |
| Composition Q | 30 | 12, <10 × 10$^1$ | <6.5 × 10$^1$ | >6.06 | 99.999 |
| Composition Q | 60 | 10, <10 | <10 | >6.88 | >99.999 |

TABLE 10

*Staphylococcus aureus* ATCC 6538

| Test Composition | Exposure Time (seconds) | Survivors (CFU/mL) | Average Survivors (CFU/mL) | Log Reduction | Percent Reduction |
|---|---|---|---|---|---|
| Composition L | 30 | 67, 55 × 10$^1$ | 6.1 × 10$^2$ | 5.40 | >99.999 |
| Composition L | 60 | 6, 5 × 10$^1$ | 5.5 × 10$^1$ | 6.44 | >99.999 |
| Composition M | 30 | 20, 18 × 10$^1$ | 1.9 × 10$^2$ | 5.91 | >99.999 |
| Composition M | 60 | <10, 2 × 10$^1$ | <1.5 × 10$^1$ | >7.01 | >99.999 |
| Composition P | 30 | 186, 200 × 10$^3$ | 1.9 × 10$^5$ | 2.56 | 99.724 |
| Composition P | 60 | 29, 19 × 10$^3$ | 2.4 × 10$^4$ | 3.46 | 99.966 |
| Composition Q | 30 | 79, 192 × 10$^1$ | 1.4 × 10$^3$ | 4.80 | 99.998 |
| Composition Q | 60 | <10, 6 × 10$^1$ | <3.5 × 10$^1$ | >6.40 | >99.999 |

As can be seen from these results, all of the test compositions achieved over a 5 log reduction at 30 and 60 seconds against *Escherichia coli* ATCC 11229. Compositions L and M achieved over a 5 log reduction at 30 and 60 seconds against *Staphylococcus aureus* ATCC 6538 while Composition Q achieved over a 5 log reduction at 60 seconds. Thus, the test compositions showed both a germicidal and detergent sanitizing action.

Example 5

A study was run to determine the effect of the chain length of the fatty acid incorporated into the test compositions. For this study, a C18 fatty acid, oleic acid, was used in a test composition. The composition tested had 4.99% potassium oleate, 1% phenylethyl proprionate, and 1% sodium citrate. The pH of each of the test solutions was adjusted to either 5.07, 8.25, 9.27, or 10.57. Water was also used as a control. The KT-90 of these test compositions at the different pH levels was measured. The results are shown in the table below:

TABLE 11

KT-90 (seconds)

| Potassium Oleate at pH 5.07 | Potassium Oleate at pH 8.25 | Potassium Oleate at pH 9.27 | Potassium Oleate at pH 10.57 |
|---|---|---|---|
| >900 | >900 | 560 | 355 |

Figure 5:
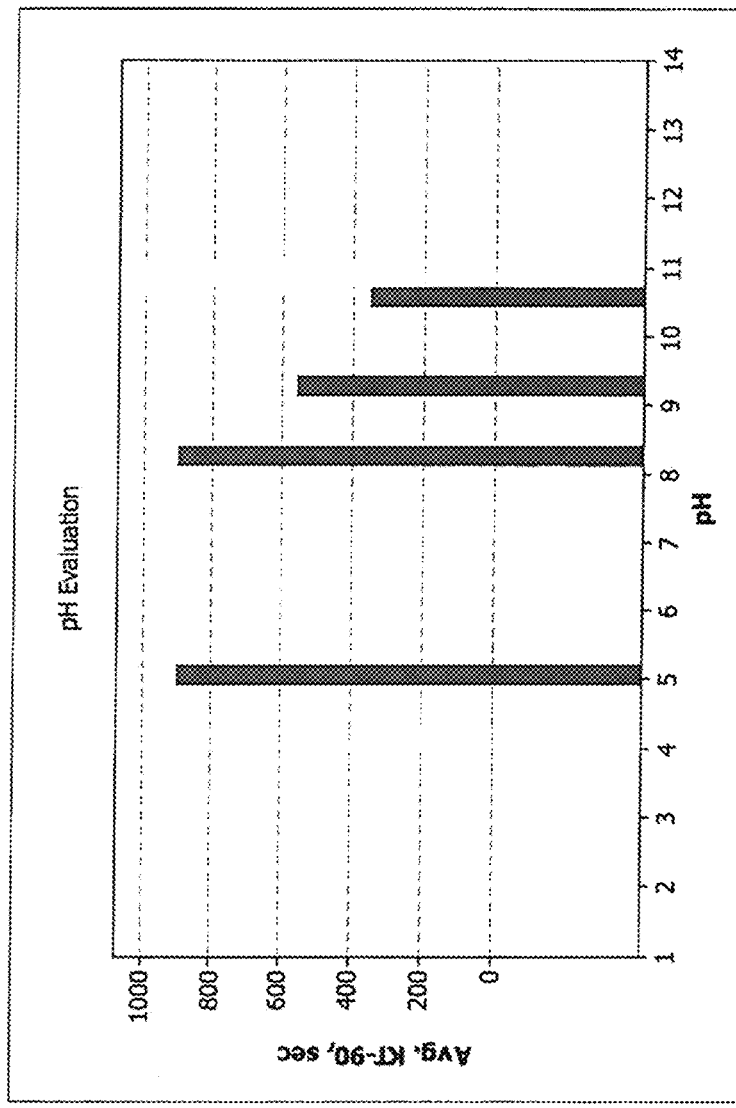
FIG. 5 is a graphical depiction of the effect of pH on the insecticidal efficacy of a long chain fatty acid soap/fatty acid mixed composition.

The results from this study are shown in FIG. 5. As can be seen from this figure, the test composition including the long chain fatty acid (oleic acid) had a 90% kill time (KT-90) of no shorter than six minutes. Although, these compositions did show a faster kill at a higher pH (pH ~10.6), the kill was still much slower (4 times as slow) as those compositions including a medium chain (C5-C12) fatty acid at a lower pH.

Example 6

Test compositions were studied for their ability to kill a variety of insects. The test compositions were directly applied to bed bugs, houseflies, fruit flies, ants and spiders. The test composition tested for these experiments included 7.25%-7.33% Fatty Acid Soap, 1% 2-phenethyl proprionate, 1% Sodium Citrate, 0.10% Xanthan Gum, 0.31% Citric Acid, and the balance as Soft Water.

(a) Bedbugs: The average percent mortality of bed bugs over 168 hours was measured. The test compositions were also compared to a commercially available insecticide, Terminix Safeshield, commercially available from Terminix.

Figure 6:
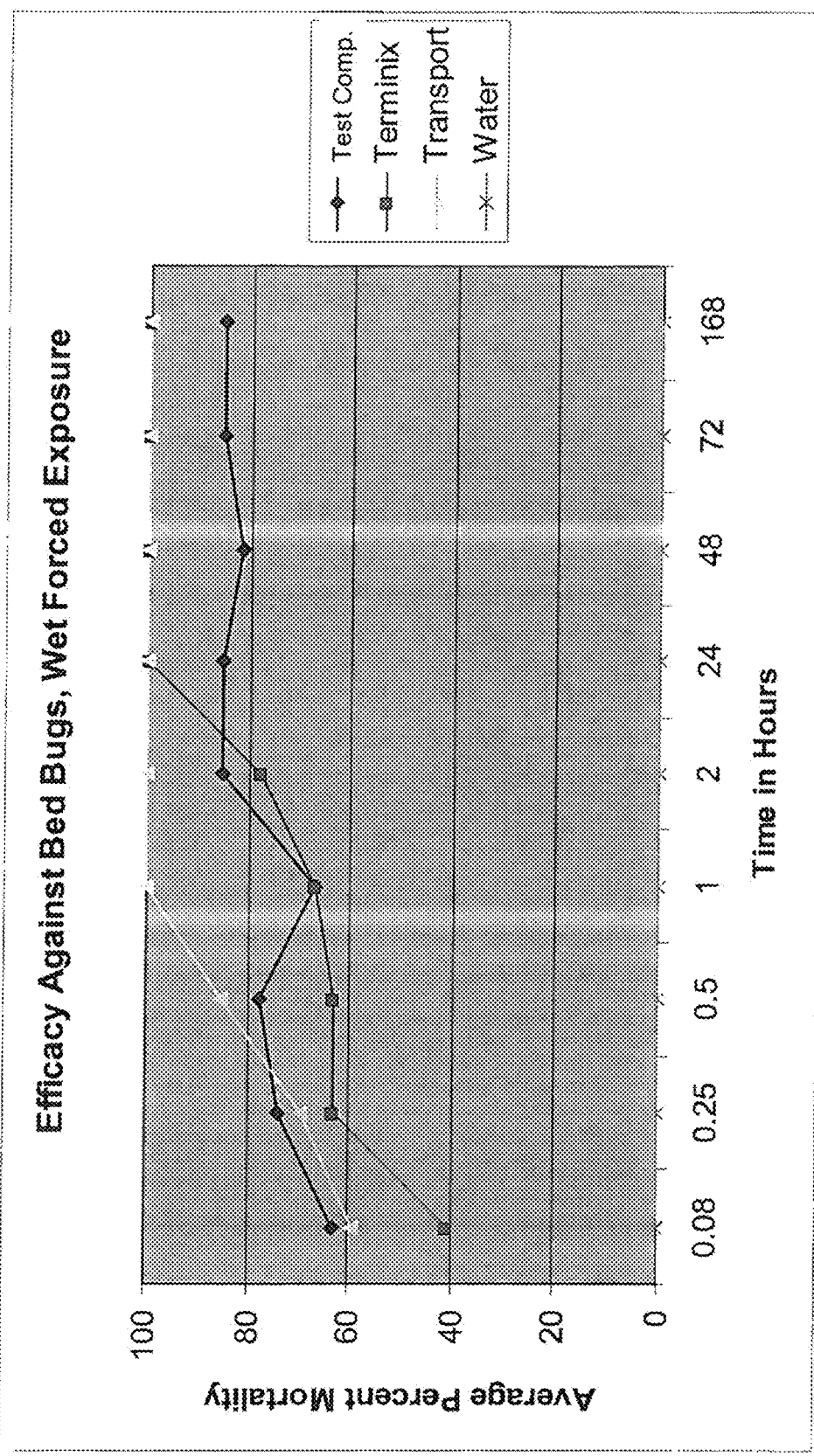
FIG. 6 is a graphical depiction of the efficacy of various compositions against bed bugs.

The results are shown in FIG. 6. As can be seen from this Figure, after about 5 minutes the test compositions had about a 60% mortality rate. This was much higher than the average mortality rate of the commercially available Terminix composition.

Figure 7:
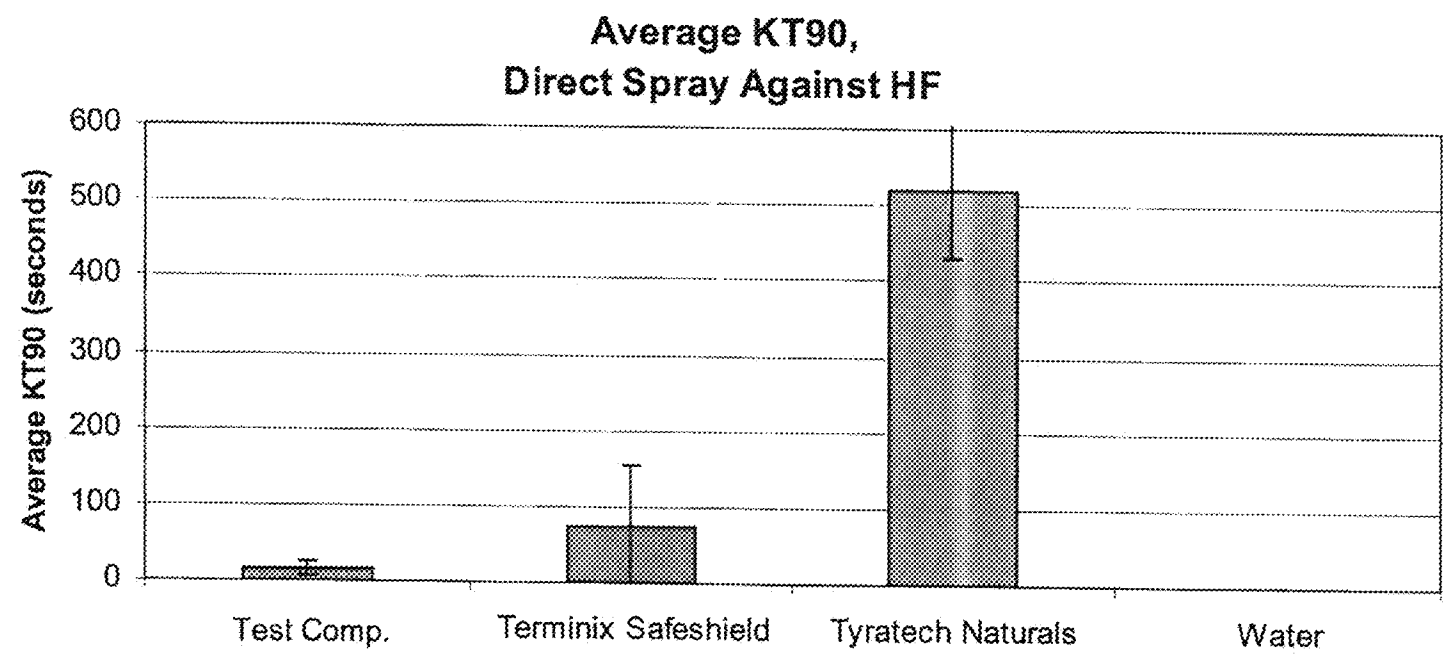

(b) Houseflies: The KT-90 of a test composition was tested against houseflies. Two other commercially available insecticides, Terminix Safeshield, and Tyratech Naturals were also tested. The results of this test are shown in FIG. 7. As can be seen from these results, the test compositions had an average KT-90 of less than 100 seconds, where as the Tyratech Naturals insecticide had a KT-90 of over 500 seconds.

Figure 8:
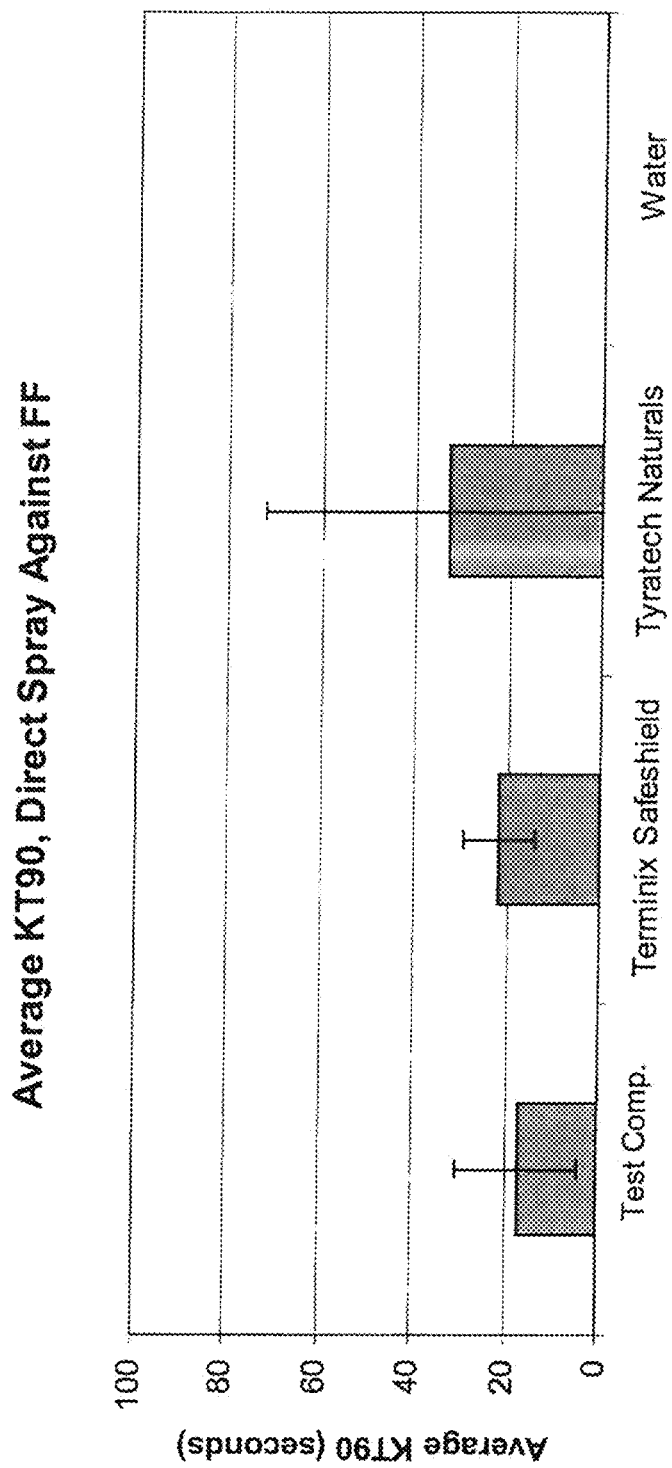
FIG. 8 is a graphical depiction of the average kill time of 90% (KT-90) of fruit flies contacted with various compositions.

(c) Fruit Flies: The KT-90 of a test composition was tested against Fruit Flies. Two other commercially available insecticides, Terminix Safeshield, and Tyratech Naturals were also tested. The results of this test are shown in FIG. 8. As can be seen from this figure, the test composition had a KT-90 of less than 20 seconds, which was faster than the KT-90 of both of the commercially available insecticides tested.

Figure 9A:
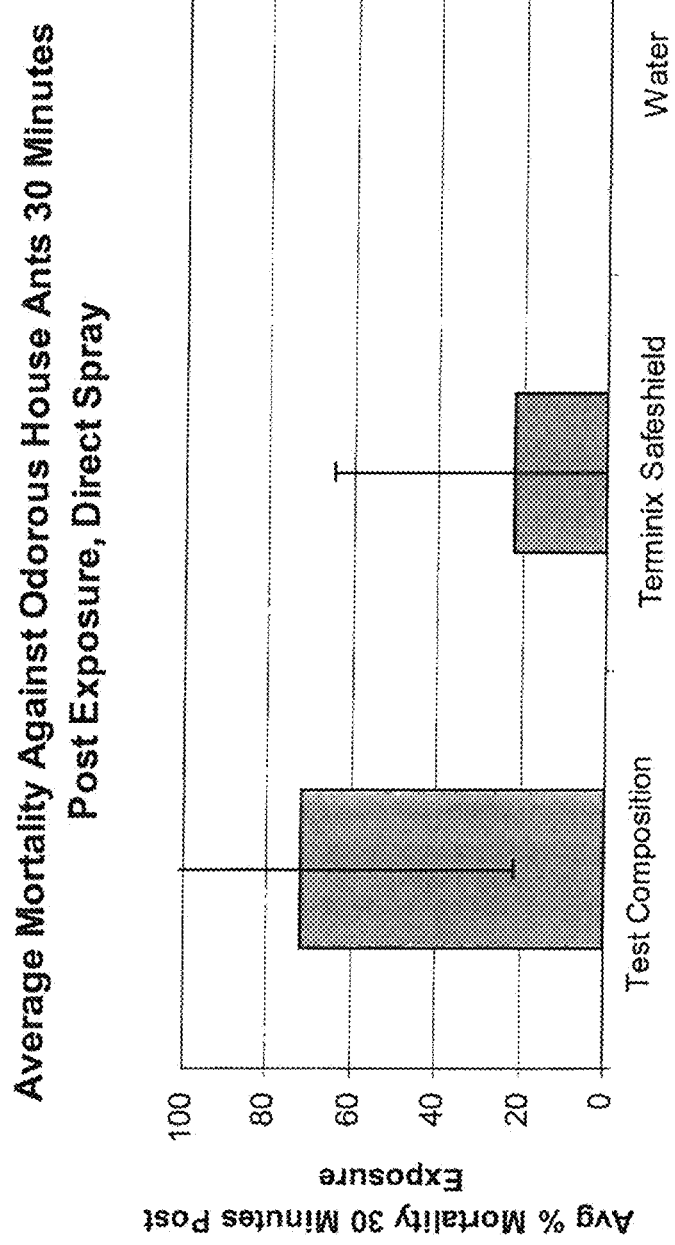
FIG. 9A is a graphical depiction of the average percent (%) mortality of house ants thirty minutes post exposure to various compositions via direct spray.
Figure 9B:
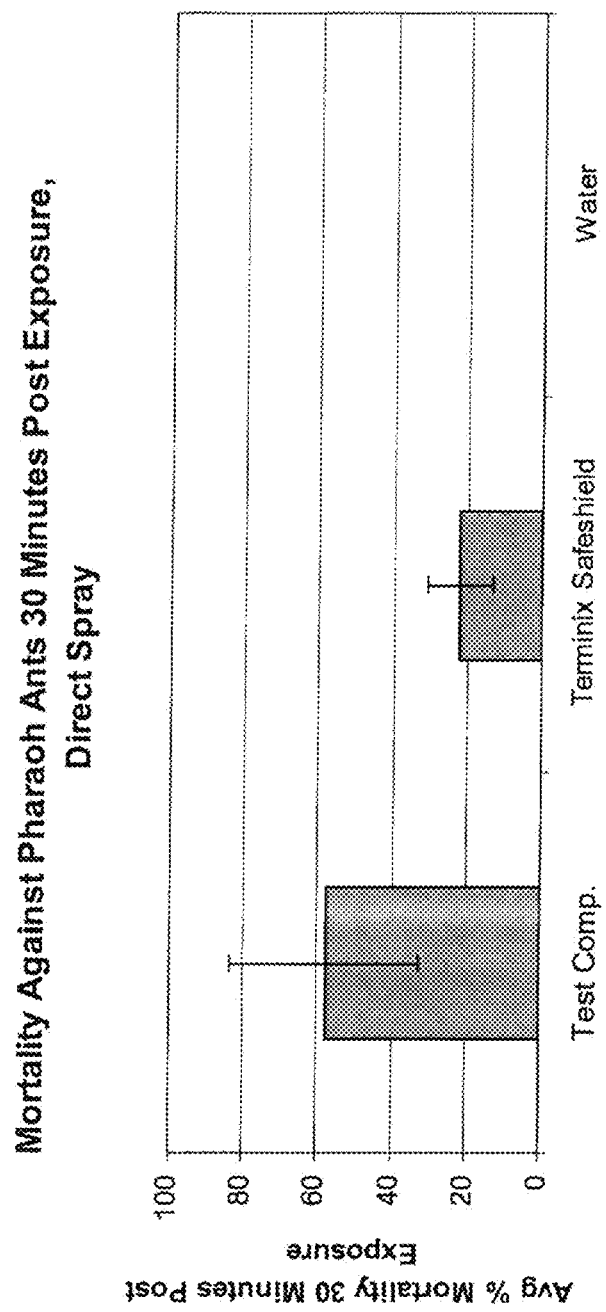
FIG. 9B is a graphical depiction of the average percent (%) mortality of pharaoh ants thirty minutes post exposure to various compositions via direct spray.
Figure 9C:
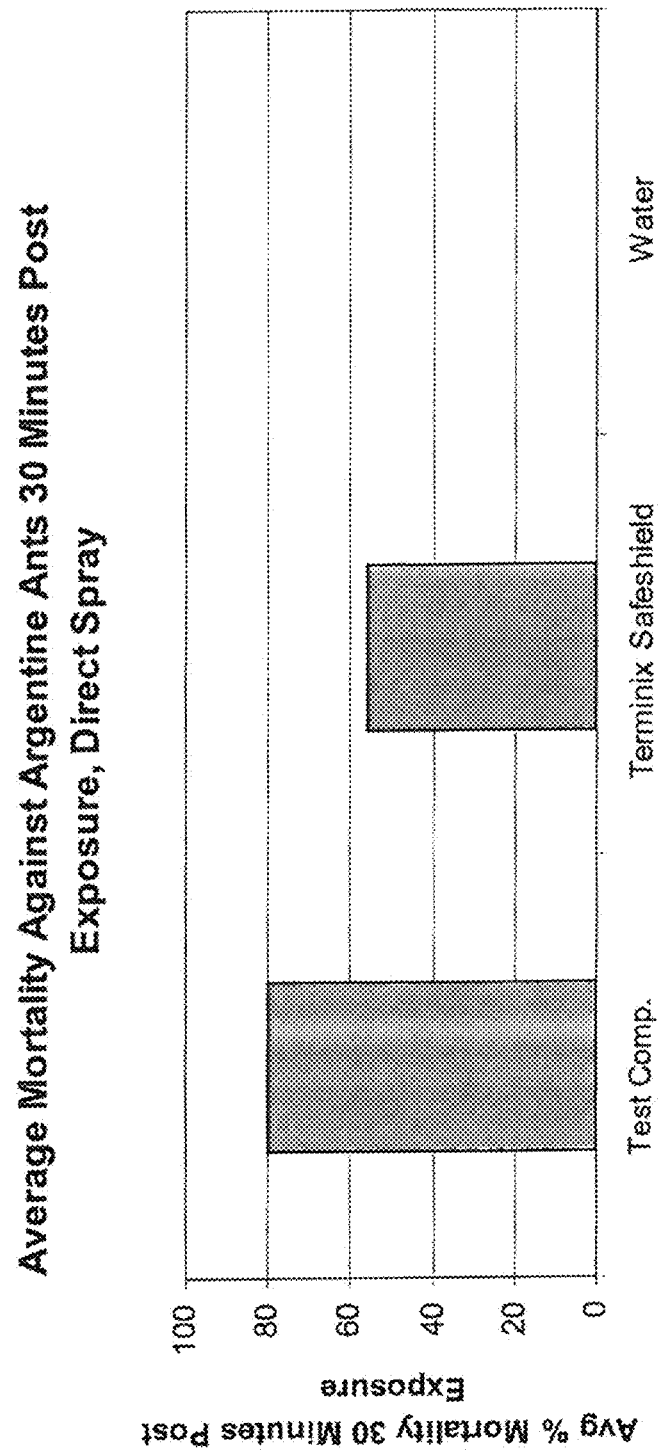
FIG. 9C is a graphical depiction of the average percent (%) mortality of argentine ants thirty minutes post exposure to various compositions via direct spray.

(d) Ants: The average mortality of house ants, pharaoh ants, and argentine ants 30 minutes post exposure to a test composition was measured. A commercially available insecticide, Terminix Safeshield, was also tested. Water was used as a control. The results from these tests are shown in FIGS. 9A, 9B, and 9C. As can be seen from these Figures, the test composition had a much higher average mortality rate thirty minutes post exposure compared to the commercially available insecticide tested.

Figure 10:
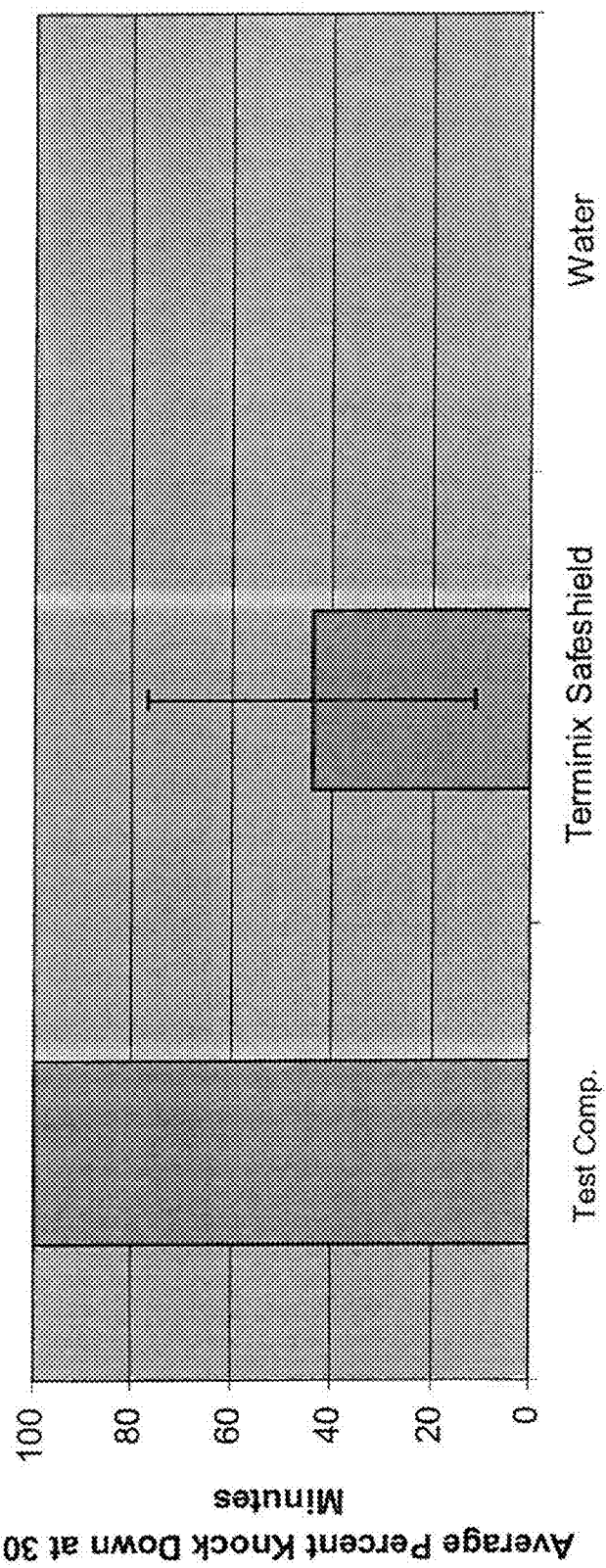
FIG. 10 is a graphical depiction of the average percent knock down of black widow spiders post exposure to various compositions via direct spray.

(e) Spiders: The average percent knock down of Black Widow spiders was measured thirty minutes post direct application of a test composition. A commercially available insecticide, Terminix Safeshield, was also tested. The results from this study are shown in FIG. 10. As can be seen from this Figure, after 30 minutes the test composition had a 100% knock down of the spiders. The commercially available insecticide had only about a 40% knock down over the same time period.

Example 7

A study was run to evaluate the preservative properties of test compositions. For this study, one 99 mL sample of the test composition was inoculated with 1 mL of a 1:1:1:1:1 mixture of bacteria and one 99 mL sample was inoculated with 1 mL of a 1:1:1 mixture of yeasts and mold. Plate counts of the samples were taken at 7, 14, 21, and 28 days.

Three test compositions were studied, one with potassium sorbate, and two without and one with a thickener. Potassium sorbate is a known preservative. The test compositions studied are shown in the table below:

TABLE 12

| Ingredient | Comp. N (wt %) | Comp. O (wt %) | Comp. Q (wt %) |
| --- | --- | --- | --- |
| Soft water | 74.00 | 73.80 | 87.74 |
| Buffer | 1.00 | 1.00 | 1.5 |
| Fatty acid | 6.00 | 6.00 | 5.90 |
| Neutralizer | 18.00 | 18.00 | 4.76 |
| 2-phenylethyl propionate | 1.00 | 1.00 | |
| Potassium Sorbate | 0.20 | | |
| Thickener | | | 0.10 |

The bacterial inoculum mixture was made up of equal parts of the following five organisms: *Staphylococcus aureus* ATCC 6538; *Escherichia coli* ATCC 11229; *Enterobacter aerogenese* ATCC 13048; *Pseudomonas aeruginosa* ATCC 15442; and *Burkholderia cepacia* ATCC 25416. The yeast and mold mixture was made up of equal parts of the following three organisms: *Candida albicans* ATCC 10231; *Saccharomyces cerevisiae* ATCC 834; and *Aspergillus niger* ATCC 16404. The tests were run at ambient temperatures, and the exposure times were 7, 14, 21, and 28 days. The results are shown in the tables below.

TABLE 13

Inoculum Numbers (CFU/mL) for Compositions N & O

| Test System | A | B | Average |
| --- | --- | --- | --- |
| Bacteria Inoculum | $56 \times 10^5$ | $51 \times 10^5$ | $5.4 \times 10^6$ |
| Yeast and Mold Inoculum | $33 \times 10^4$ | $37 \times 10^4$ | $3.4 \times 10^5$ |

TABLE 13a

Inoculum Numbers (CFU/mL) for Composition Q

| Test System | A | B | C | Average |
| --- | --- | --- | --- | --- |
| Bacterial Inoculum | $50 \times 10^5$ | $49 \times 10^5$ | $23 \times 10^5$ | $4.1 \times 10^6$ |
| Yeast and Mold Inoculum | $9 \times 10^4$ | $14 \times 10^4$ | $16 \times 10^4$ | $1.3 \times 10^5$ |

TABLE 14

Bacteria

| Test Composition | Pre-Inoculum Sterility Check (CFU/mL) | Day 7 Survivors (CFU/mL) | Day 14 Survivors (CFU/mL) | Day 21 Survivors (CFU/mL) | Day 28 Survivors (CFU/mL) |
| --- | --- | --- | --- | --- | --- |
| N | <1 | <10 | <10 | <10 | <10 |
| O | <1 | <10 | <10 | <10 | <10 |
| Q | <1 | <10 | <10 | <10 | <10 |

TABLE 15

Yeast and Mold

| Test Composition | Pre-Inoculum Sterility Check (CFU/mL) | Day 7 Survivors (CFU/mL) | Day 14 Survivors (CFU/mL) | Day 21 Survivors (CFU/mL) | Day 28 Survivors (CFU/mL) |
| --- | --- | --- | --- | --- | --- |
| N | <1 | <100 | <100 | <100 | <100 |
| O | <1 | <100 | <100 | <100 | <100 |
| Q | <1 | <100 | <100 | <100 | <100 |

As can be seen from these results, all of the test compositions passed the preservation criteria following the *United States Pharmacopeia* guidelines with regard to bacteria and yeast and mold.

Example 8

Test Compositions M and P from Example 4 were diluted and evaluated for their food contact sanitizing ability. In particular, the diluted test compositions were evaluated against *Escherichia coli* ATCC 11229 and *Staphylococcus aureus* ATCC 6538. Compositions M and P are shown again in the table below for convenience.

TABLE 16

| Ingredient | Comp. M (wt %) | Comp. P (wt %) |
| --- | --- | --- |
| Soft water | 87.24 | 88.06 |
| Buffer | 1.36 | 1.51 |
| Fatty acid | 6.00 | 5.99 |
| Neutralizer | 4.30 | 4.34 |
| 2-phenylethyl propionate | 1.00 | |
| Thickener | | 0.10 |

Composition M was diluted to prepare four different test dilutions as follows:

TABLE 17

| Test Substance | Concentration | Diluent | mL of Test Substance | mL of Diluent |
|---|---|---|---|---|
| Composition M | 1:2 | Sterile Milli-Q Water | 100 | 100 |
|  | 1:4 |  | 50 | 150 |
|  | 1:8 |  | 25 | 175 |
|  | 1:16 |  | 12.5 | 187.5 |

Composition P was diluted to four different test dilutions with di-ionized water as follows:

TABLE 17a

| Test Substance | Concentration |
|---|---|
| Composition P | 1:2 |
|  | 1:4 |
|  | 1:8 |
|  | 1:16 |

The compositions were tested against *Escherichia coli* ATCC 11229 and *Staphylococcus aureus* ATCC 6538, at ambient temperature for 30 and 60 second exposure times. The results are shown below.

TABLE 18

Inoculum Numbers (CFU/mL) for Composition M

| Test System | A | B | Average |
|---|---|---|---|
| *Escherichia coli* ATCC 11229 | $143 \times 10^6$ | $168 \times 10^6$ | $1.6 \times 10^8$ |
| *Staphylococcus aureus* ATCC 6538 | $42 \times 10^6$ | $45 \times 10^6$ | $4.4 \times 10^7$ |

TABLE 18a

Inoculum Numbers (CFU/ml) for Composition P

| Test System | A | B | Average |
|---|---|---|---|
| *Escherichia coli* ATCC 11229 | $198 \times 10^6$ | $190 \times 10^6$ | $1.9 \times 10^8$ |
| *Staphylococcus aureus* ATCC 6538 | $63 \times 10^6$ | $77 \times 10^6$ | $7.0 \times 10^7$ |

TABLE 19

*Escherichia coli* ATCC 11229

| | Exposure Time | Survivors (CFU/mL) | Average Survivors (CFU/mL) | Log Reduction | Percent Reduction |
|---|---|---|---|---|---|
| Composition M Dilution | | | | | |
| 1:2 | 30 seconds | <10, <10 | <10 | >7.19 | >99.999 |
|  | 60 seconds | <10, <10 | <10 | >7.19 | >99.999 |
| 1:4 | 30 seconds | <10, <10 | <10 | >7.19 | >99.999 |
|  | 60 seconds | <10, <10 | <10 | >7.19 | >99.999 |
| 1:8 | 30 seconds | <10, <10 | <10 | >7.19 | >99.999 |
|  | 60 seconds | <10, <10 | <10 | >7.19 | >99.999 |
| 1:16 | 30 seconds | <10, $95 \times 10^1$ | $4.8 \times 10^2$ | 5.51 | >99.999 |
|  | 60 seconds | <10, <10 | <10 | >7.19 | >99.999 |
| Composition P Dilution | | | | | |
| 1:2 | 30 seconds | <10, <10 | <10 | >7.29 | >99.999 |
|  | 60 seconds | <10, <10 | <10 | >7.29 | >99.999 |
| 1:4 | 30 seconds | <10, <10 | <10 | >7.29 | >99.999 |
|  | 60 seconds | <10, <10 | <10 | >7.29 | >99.999 |
| 1:8 | 30 seconds | 280*, 348* $\times 10^5$ | $3.1 \times 10^7$ | 0.79 | 83.814 |
|  | 60 seconds | 50, $83 \times 10^5$ | $6.6 \times 10^6$ | 1.46 | 96.572 |
| 1:16 | 30 seconds | 969*, 1425* $\times 10^5$ | $1.2 \times 10^8$ | 0.21 | 38.299 |
|  | 60 seconds | 1425*, 1529*, $\times 10^5$ | $1.5 \times 10^8$ | 0.12 | 23.608 |

*Estimated count

TABLE 20

*Staphylococcus aureus* ATCC 6538

| | Exposure Time | Survivors (CFU/mL) | Average Survivors (CFU/mL) | Log Reduction | Percent Reduction |
|---|---|---|---|---|---|
| Composition M Dilution | | | | | |
| 1:2 | 30 seconds | 496*, 632* $\times 10^1$ | $5.6 \times 10^3$ | 3.89 | 99.987 |
|  | 60 seconds | 16, $26 \times 10^1$ | $2.1 \times 10^2$ | 5.32 | >99.999 |
| 1:4 | 30 seconds | 51, $23 \times 10^3$ | $3.7 \times 10^4$ | 3.07 | 99.915 |
|  | 60 seconds | 708*, 524* $\times 10^1$ | $6.2 \times 10^3$ | 3.85 | 99.986 |
| 1:8 | 30 seconds | 248, $172 \times 10^1$ | $2.1 \times 10^3$ | 4.32 | 99.995 |
|  | 60 seconds | 4, $6 \times 10^1$ | $5.0 \times 10^1$ | 5.94 | >99.999 |
| 1:16 | 30 seconds | 1596*, 1197* $\times 10^1$ | $1.4 \times 10^4$ | 3.49 | 99.968 |
|  | 60 seconds | 149, $40 \times 10^1$ | $9.4 \times 10^2$ | 4.66 | 99.998 |

TABLE 20-continued

Staphylococcus aureus ATCC 6538

| | Exposure Time | Survivors (CFU/mL) | Average Survivors (CFU/mL) | Log Reduction | Percent Reduction |
|---|---|---|---|---|---|
| Composition P Dilution | | | | | |
| 1:2 | 30 seconds | 348*, 404*, ×10$^3$ | 3.8 × 10$^5$ | 2.27 | 99.463 |
| | 60 seconds | 50, 53 × 10$^3$ | 5.2 × 10$^4$ | 3.13 | 99.926 |
| 1:4 | 30 seconds | 57, 72 × 10$^5$ | 6.5 × 10$^6$ | 1.04 | 90.786 |
| | 60 seconds | 24, 18 × 10$^5$ | 2.1 × 10$^6$ | 1.52 | 97.000 |
| 1:8 | 30 seconds | 560*, 524* × 10$^5$ | 5.4 × 10$^7$ | 0.11 | 22.571 |
| | 60 seconds | 472*, 484* × 10$^5$ | 4.8 × 10$^7$ | 0.17 | 31.714 |
| 1:16 | 30 seconds | 532*, 444* × 10$^5$ | 4.9 × 10$^7$ | 0.16 | 30.286 |
| | 60 seconds | 444*, 396* × 10$^5$ | 4.2 × 10$^7$ | 0.22 | 40.000 |

*Estimated count

As can be seen from these results, all of the dilutions of Composition M achieved over a 5 log reduction at 30 and 60 seconds against *Escherichia coli* ATCC 11229. Composition P was able to achieve over a 5 log reduction at 30 and 60 seconds against *Escherichia coli* ATCC 11229 at 50% and 25% dilutions.
Composition M was able to achieve over a 5 log reduction at 60 seconds against and *Staphylococcus aureus* ATCC 6538 at the 1:2 and 1:8 dilutions. Composition P was unable to achieve over a 5 log reduction at 60 seconds against *Staphylococcus aureus* ATCC 6538 at any dilution tested.

Example 9

Test compositions were evaluated for Use Dilution Disinfectant efficacy and Germicidal Spray Disinfectant efficacy. In particular the test compositions were evaluated against *Staphylococcus aureus* ATCC 6538 and *Pseudomonas aeruginosa* ATCC 15442. Composition P was used for these tests. Composition P is shown again for convenience.

| Ingredient | Comp. P (wt %) |
|---|---|
| Soft water | 88.06 |
| Buffer | 1.51 |
| Fatty acid | 5.99 |
| Neutralizer | 4.34 |
| 2-phenylethyl propionate | |
| Thickener | 0.10 |

The composition was tested against *Staphylococcus aureus* ATCC 6538 and *Pseudomonas aeruginosa* ATCC 15442, at ambient temperature for five minutes for both tests. The spray distance was 6-8 inches with three trigger pulls with an average weight per spray of 2.3 grams for the Germicidal Spray disinfectant efficacy test.

The results of the Use Dilution Disinfectant efficacy are shown below.

TABLE 21

Test Results:

| Test Substance | Test System | # Negative Tubes/# carriers Tested | Pass/Fail* |
|---|---|---|---|
| Composition P | *Staphylococcus aureus* ATCC 6538 | 2/60 | Fail |

TABLE 21-continued

Test Results:

| Test Substance | Test System | # Negative Tubes/# carriers Tested | Pass/Fail* |
|---|---|---|---|
| | *Pseudomonas aeruginosa* ATCC 15442 | 44/60 | Fail |

*The EPA standard for disinfectants is 59/60 negative carriers.

TABLE 22

Test Controls

| Test Substance | Test System | # Negative Tubes/# carriers Tested |
|---|---|---|
| Positive Carriers | *Staphylococcus aureus* ATCC 6538 | 1 positive of 1 tested |
| | *Pseudomonas aeruginosa* ATCC 15442 | 1 positive of 1 tested |
| Negative Carrier | Not Applicable | 1 negative of 1 tested |
| Carrier Enumeration | *Staphylococcus aureus* ATCC 6538 | 4.2 × 10$^6$ CFU/Carrier |
| | *Pseudomonas aeruginosa* ATCC 15442 | 1.9 × 10$^7$ CFU/Carrier |

For a composition to pass the Use Dilution test, at least 59 of the 60 tubes tested were required to be negative for each organism tested. Composition P did not pass Use Dilution test for *Staphylococcus aureus* ATCC 6538 or *Pseudomonas aeruginosa* ATCC 15442 at 5 minutes.

The results of the Germicidal Spray Disinfectant efficacy are shown below:

TABLE 23

Test Results:

| Test Substance | Test System | # Negative Tubes/# carriers Tested | Pass/Fail* |
|---|---|---|---|
| Composition P | *Staphylococcus aureus* ATCC 6538 | 20/60 | Fail |
| | *Pseudomonas aeruginosa* ATCC 15442 | 60/60 | Pass |

*The EPA standard for disinfectants is 59/60 negative carriers.

TABLE 24

| | Test Controls | |
|---|---|---|
| Test Substance | Test System | # Negative Tubes/# carriers Tested |
| Positive Carriers | Staphylococcus aureus ATCC 6538 | 2 positive of 2 tested |
| | Pseudomonas aeruginosa ATCC 15442 | 2 positive of 2 tested |
| Negative Carrier | Not Applicable | 1 negative of 1 tested |
| Carrier Enumeration | Staphylococcus aureus ATCC 6538 | $8.0 \times 10^4$ CFU/Carrier |
| | Pseudomonas aeruginosa ATCC 15442 | $1.8 \times 10^5$ CFU/Carrier |

Composition P failed the Germicidal Spray Disinfectants test for Pseudomonas aeruginosa ATCC 15442 at 5 minutes, and failed Staphylococcus aureus ATCC 6538 at 5 minutes.

The invention claimed is:

1. An insecticidal composition comprising:
   (a) about 1.0 wt. % to about 7.0 wt. % of a fatty acid including a branched or straight chain C5 to C11 fatty acid
   (b) about 1.0 wt. % to about 7.0 wt. % of a neutralizer including an alkali metal hydroxide, amine, alkanolamine, and mixtures thereof;
   (c) about 0.1 wt. % to about 1.0 wt. % of a buffer including citrate, citric acid and mixtures thereof;
   (d) at least about 80 wt. % of a carrier, wherein the composition has a pH of about 7.5 to about 9.0; and
   wherein the fatty acid and neutralizer form a fatty acid soap in an amount between about 5 wt. % and about 8 wt. %.

2. The composition of claim 1, wherein the fatty acid is selected from the group consisting of hexanoic acid, heptanoic acid, octanoic acid, nonanoic acid, decanoic acid, lauric acid and mixtures thereof.

3. The composition of claim 1, wherein the neutralizer comprises an alkali metal hydroxide.

4. The composition of claim 3, wherein the alkali metal hydroxide is selected from the group consisting of sodium hydroxide, potassium hydroxide, and mixtures thereof.

5. The composition of claim 1, wherein the neutralizer comprises monoethanolamine, diethanolamine, triethanolamine, monoisopropanolamine, monoisopropylamine, isopropylamine, n-propylamine, diethyleneamine, triethylamine, n-butylamine, isobutylamine, cyclohexylamine, and mixtures thereof.

6. The composition of claim 1, wherein the buffer is selected from citrate, citric acid, a bicarbonate, and mixtures thereof.

7. The composition of claim 1, wherein the carrier comprises water, and wherein the ingredients in the composition are suitable for human consumption.

8. The composition of claim 1, wherein the composition comprises:
   (a) about 3 wt. % to about 4 wt. % of the fatty acid;
   (b) about 3 wt. % to about 4 wt. % of the neutralizer including of an alkali metal hydroxide, amine, alkanolamine, and mixtures thereof;
   (c) about 0.1 wt. % to about 1.0 wt. % of the buffer;
   (d) at least about 80 wt. % of the carrier; and
   wherein the fatty acid and neutralizer form a fatty acid soap in an amount of about 7 wt. %; and
   wherein the composition is substantially free of C14 to C24 fatty acids.

9. The composition of claim 1, further comprising a thickening agent selected from xanthan gum, guar gum, polyethylene oxide, polyvinyl pyrrolidone, polyvinyl alcohol, clay thickener, betonite, carboxyl methyl ether cellulose, kaolin, soy protein and mixtures thereof.

10. The composition of claim 1, further comprising an additional ingredient selected from an insecticide, an essential oil, 2-phenyl ethyl propionate, a residual insecticide, and mixtures thereof.

11. The composition of claim 1, wherein the pH is about 8.0 to about 8.5.

12. The composition of claim 1, wherein the fatty acid comprises decanoic acid, and the neutralizing agent comprises potassium hydroxide.

13. A method of reducing a population of microorganism on an object, said method comprising applying a composition comprising
   (a) about 1.0 wt, % to about 7.0 wt. % of a fatty acid including a branched or straight chain C5 to C11 fatty acid
   (b) about 1.0 wt. % to about 7.0 wt. % of a neutralizer including an alkali metal hydroxide, amine, alkanolamine, and mixtures thereof;
   (c) about 0.1 wt. % to about 1.0 wt. % of a buffer including citrate, citric acid, and mixtures thereof; and
   (d) at least about 80 wt. % of a carrier, wherein the composition has a pH of about 7.5 to about 9.0;
   wherein the fatty acid and neutralizer form a fatty acid soap in an amount between about 5 wt. % and about 8 wt. %.

14. The method of claim 13, wherein the fatty acid is selected from the group consisting of hexanoic acid, heptanoic acid, octanoic acid, nonanoic acid, decanoic acid, lauric acid and mixtures thereof.

15. The method of claim 13, wherein the neutralizer comprises an alkali metal hydroxide.

16. The method of claim 15, wherein the alkali metal hydroxide is selected from the group consisting of sodium hydroxide, potassium hydroxide, and mixtures thereof.

17. The method of claim 13, wherein the neutralizer comprises monoethanolamine, diethanolamine, triethanolamine, monoisoproanolamine, monoisopropylamine, isopropylamine, n-propylamine, diethyleneamine, triethylamine, n-butylamine, isobutylamine, cyclohexylamine, and mixtures thereof.

18. The method of claim 13, further comprising a thickening agent selected from xanthan gum, guar gum, polyethylene oxide, polyvinyl pyrrolidone, polyvinyl alcohol, clay thickener, betonite, carboxyl methyl ether cellulose, kaolin, soy protein and mixtures thereof.

19. The method of claim 15, wherein the buffer is selected from citrate, citric acid, a bicarbonate, and mixtures thereof.

20. A method of removing a food soil from a surface, said method comprising applying the composition of claim 8 to the surface, wherein the composition has a pH of about 7.5 to about 9.0.

* * * * *